US011793563B2

(12) United States Patent
Benamou et al.

(10) Patent No.: US 11,793,563 B2
(45) Date of Patent: Oct. 24, 2023

(54) ARTHROSCOPIC DEVICES AND METHODS

(71) Applicant: Relign Corporation, Campbell, CA (US)

(72) Inventors: Steffan Benamou, Morgan Hill, CA (US); Aaron Germain, San Jose, CA (US); Michael D Walker, San Francisco, CA (US); Simon Malkevich, Gilroy, CA (US); Jacob Tonkel, San Jose, CA (US)

(73) Assignee: Relign Corporation, Campbell, CA (US)

( * ) Notice: Subject to any disclaimer, the term of this patent is extended or adjusted under 35 U.S.C. 154(b) by 101 days.

(21) Appl. No.: 17/576,560

(22) Filed: Jan. 14, 2022

(65) Prior Publication Data

US 2022/0133394 A1 May 5, 2022

Related U.S. Application Data

(63) Continuation of application No. 15/495,620, filed on Apr. 24, 2017, now Pat. No. 11,253,311.
(Continued)

(51) Int. Cl.
*A61B 18/14* (2006.01)
*A61B 17/32* (2006.01)
(Continued)

(52) U.S. Cl.
CPC ........ *A61B 18/14* (2013.01); *A61B 17/32002* (2013.01); *A61B 18/148* (2013.01);
(Continued)

(58) Field of Classification Search
CPC .......... A61B 17/320016; A61B 18/148; A61B 2018/0091; A61B 2017/00876; A61B 2017/0046; A61B 18/14
See application file for complete search history.

(56) References Cited

U.S. PATENT DOCUMENTS 3,903,891 A 9/1975 Brayshaw
4,428,748 A 1/1984 Peyman et al.
(Continued)

FOREIGN PATENT DOCUMENTS

CN 2766785 Y 3/2006
CN 1977194 A 6/2007
(Continued)

OTHER PUBLICATIONS

"U.S. Appl. No. 12/541,043, Final Office Action dated Sep. 28, 2012", 6 pgs.
(Continued)

*Primary Examiner* — Linda C Dvorak
*Assistant Examiner* — Ryan T Clark
(74) *Attorney, Agent, or Firm* — SCHWEGMAN LUNDBERG & WOESSNER, P.A.

(57) ABSTRACT

An arthroscopic or other surgical system includes a handpiece and a probe. The handpiece carries a motor drive, and the probe has a proximal hub and an elongate shaft which extends about a longitudinal axis to a working end of the probe. The hub is configured for detachably coupling to the handpiece, and the motor drive is configured to couple to a rotating drive coupling in the hub when the hub is coupled to the handpiece. A first magnetic component is carried by the hub, and a second magnetic component is coupled to rotate with the rotating drive coupling.

16 Claims, 7 Drawing Sheets

Related U.S. Application Data

(60) Provisional application No. 62/326,544, filed on Apr. 22, 2016.

(51) Int. Cl.
  *A61B 90/90* (2016.01)
  *A61B 90/98* (2016.01)
  *A61B 18/00* (2006.01)
  *A61B 17/00* (2006.01)
  *A61B 90/00* (2016.01)

(52) U.S. Cl.
  CPC ........ *A61B 18/149* (2013.01); *A61B 18/1442* (2013.01); *A61B 90/90* (2016.02); *A61B 90/98* (2016.02); *A61B 2017/00017* (2013.01); *A61B 2017/0046* (2013.01); *A61B 2017/00482* (2013.01); *A61B 2017/00876* (2013.01); *A61B 2018/0091* (2013.01); *A61B 2018/00178* (2013.01); *A61B 2018/00196* (2013.01); *A61B 2018/00202* (2013.01); *A61B 2018/00577* (2013.01); *A61B 2018/00589* (2013.01); *A61B 2018/1422* (2013.01); *A61B 2090/0811* (2016.02)

(56) References Cited

U.S. PATENT DOCUMENTS

| | | |
|---|---|---|
| 4,949,718 A | 8/1990 | Neuwirth et al. |
| 4,979,948 A | 12/1990 | Geddes et al. |
| 5,045,056 A | 9/1991 | Behl |
| 5,078,717 A | 1/1992 | Parins et al. |
| 5,084,044 A | 1/1992 | Quint |
| 5,085,659 A | 2/1992 | Rydell |
| 5,191,883 A | 3/1993 | Lennox et al. |
| 5,197,963 A | 3/1993 | Parins |
| 5,242,390 A | 9/1993 | Goldrath |
| 5,248,312 A | 9/1993 | Langberg |
| 5,269,794 A | 12/1993 | Rexroth |
| 5,277,201 A | 1/1994 | Stern |
| 5,282,799 A | 2/1994 | Rydell |
| 5,324,254 A | 6/1994 | Phillips |
| 5,344,435 A | 9/1994 | Turner et al. |
| 5,374,261 A | 12/1994 | Yoon |
| 5,401,272 A | 3/1995 | Perkins |
| 5,401,274 A | 3/1995 | Kusunoki |
| 5,429,136 A | 7/1995 | Milo et al. |
| 5,441,498 A | 8/1995 | Perkins |
| 5,443,470 A | 8/1995 | Stern et al. |
| 5,456,689 A | 10/1995 | Kresch et al. |
| 5,492,527 A | 2/1996 | Glowa et al. |
| 5,496,314 A | 3/1996 | Eggers |
| 5,501,681 A | 3/1996 | Neuwirth et al. |
| 5,505,730 A | 4/1996 | Edwards |
| 5,507,725 A | 4/1996 | Savage et al. |
| 5,558,672 A | 9/1996 | Edwards et al. |
| 5,562,703 A | 10/1996 | Desai |
| 5,562,720 A | 10/1996 | Stern et al. |
| 5,575,788 A | 11/1996 | Baker et al. |
| 5,584,872 A | 12/1996 | Lafontaine et al. |
| 5,592,727 A | 1/1997 | Glowa et al. |
| 5,622,647 A | 4/1997 | Kerr et al. |
| 5,647,848 A | 7/1997 | Slashed |
| 5,653,684 A | 8/1997 | Laptewicz et al. |
| 5,653,692 A | 8/1997 | Masterson et al. |
| 5,662,647 A | 9/1997 | Crow et al. |
| 5,672,174 A | 9/1997 | Gough et al. |
| 5,681,308 A | 10/1997 | Edwards et al. |
| 5,697,281 A | 12/1997 | Eggers et al. |
| 5,697,882 A | 12/1997 | Eggers et al. |
| 5,713,942 A | 2/1998 | Stern et al. |
| 5,733,298 A | 3/1998 | Berman et al. |
| 5,749,885 A * | 5/1998 | Sjostrom .......... A61B 17/32002 606/180 |
| 5,769,846 A | 6/1998 | Edwards et al. |
| 5,769,880 A | 6/1998 | Truckai et al. |
| 5,779,662 A | 7/1998 | Berman |
| 5,800,493 A | 9/1998 | Stevens et al. |
| 5,810,802 A | 9/1998 | Panescu et al. |
| 5,827,273 A | 10/1998 | Edwards |
| 5,843,020 A | 12/1998 | Tu et al. |
| 5,846,239 A | 12/1998 | Swanson et al. |
| 5,860,974 A | 1/1999 | Abele |
| 5,866,082 A | 2/1999 | Hatton et al. |
| 5,876,340 A | 3/1999 | Tu et al. |
| 5,879,347 A | 3/1999 | Saadat |
| 5,891,094 A | 4/1999 | Masterson et al. |
| 5,891,134 A | 4/1999 | Goble et al. |
| 5,891,136 A | 4/1999 | McGee et al. |
| 5,902,251 A | 5/1999 | Vanhooydonk et al. |
| 5,904,651 A | 5/1999 | Swanson et al. |
| 5,925,038 A | 7/1999 | Panescu et al. |
| 5,954,714 A | 9/1999 | Saadat et al. |
| 5,964,755 A | 10/1999 | Edwards |
| 5,976,129 A | 11/1999 | Desai |
| 5,980,515 A | 11/1999 | Tu |
| 5,997,534 A | 12/1999 | Tu et al. |
| 6,024,743 A | 2/2000 | Edwards |
| 6,026,331 A | 2/2000 | Feldberg et al. |
| 6,037,724 A | 3/2000 | Buss et al. |
| 6,041,260 A | 3/2000 | Stern et al. |
| 6,053,909 A | 4/2000 | Shadduck |
| 6,057,689 A | 5/2000 | Saadat |
| 6,086,581 A | 7/2000 | Reynolds et al. |
| 6,091,993 A | 7/2000 | Bouchier et al. |
| 6,113,597 A | 9/2000 | Eggers et al. |
| 6,136,014 A | 10/2000 | Sirimanne et al. |
| 6,139,570 A | 10/2000 | Saadat et al. |
| 6,146,378 A | 11/2000 | Mikus et al. |
| 6,149,620 A | 11/2000 | Baker et al. |
| 6,214,003 B1 | 4/2001 | Morgan et al. |
| 6,228,078 B1 | 5/2001 | Eggers et al. |
| 6,254,599 B1 | 7/2001 | Lesh et al. |
| 6,283,962 B1 | 9/2001 | Tu et al. |
| 6,296,639 B1 | 10/2001 | Truckai et al. |
| 6,302,904 B1 | 10/2001 | Wallsten et al. |
| 6,315,776 B1 | 11/2001 | Edwards et al. |
| 6,366,818 B1 | 4/2002 | Bolmsjo |
| 6,387,088 B1 | 5/2002 | Shattuck et al. |
| 6,395,012 B1 | 5/2002 | Yoon |
| 6,409,722 B1 | 6/2002 | Hoey et al. |
| 6,416,508 B1 | 7/2002 | Eggers et al. |
| 6,416,511 B1 | 7/2002 | Lesh et al. |
| 6,443,947 B1 | 9/2002 | Marko et al. |
| 6,491,690 B1 | 12/2002 | Goble et al. |
| 6,508,815 B1 | 1/2003 | Strul et al. |
| 6,551,310 B1 | 4/2003 | Ganz et al. |
| 6,565,561 B1 | 5/2003 | Goble et al. |
| 6,589,237 B2 | 7/2003 | Woloszko et al. |
| 6,602,248 B1 | 8/2003 | Sharps et al. |
| 6,607,545 B2 | 8/2003 | Kammerer et al. |
| 6,622,731 B2 | 9/2003 | Daniel et al. |
| 6,635,054 B2 | 10/2003 | Fjield et al. |
| 6,635,055 B1 | 10/2003 | Cronin |
| 6,663,626 B2 | 12/2003 | Truckai et al. |
| 6,673,071 B2 | 1/2004 | Vandusseldorp et al. |
| 6,699,241 B2 | 3/2004 | Rappaport et al. |
| 6,726,684 B1 | 4/2004 | Woloszko et al. |
| 6,736,811 B2 | 5/2004 | Panescu et al. |
| 6,746,447 B2 | 6/2004 | Davison et al. |
| 6,758,847 B2 | 7/2004 | Maguire |
| 6,780,178 B2 | 8/2004 | Palanker et al. |
| 6,802,839 B2 | 10/2004 | Behl |
| 6,813,520 B2 | 11/2004 | Truckai et al. |
| 6,814,730 B2 | 11/2004 | Li |
| 6,832,996 B2 | 12/2004 | Woloszko et al. |
| 6,837,887 B2 | 1/2005 | Woloszko et al. |
| 6,837,888 B2 | 1/2005 | Ciarrocca et al. |
| 6,840,935 B2 | 1/2005 | Lee |
| 6,872,205 B2 | 3/2005 | Lesh et al. |
| 6,896,674 B1 | 5/2005 | Woloszko et al. |
| 6,905,497 B2 | 6/2005 | Truckai et al. |
| 6,923,805 B1 | 8/2005 | Lafontaine et al. |

(56) References Cited

U.S. PATENT DOCUMENTS

| | | |
|---|---|---|
| 6,929,642 B2 | 8/2005 | Xiao et al. |
| 6,949,096 B2 | 9/2005 | Davison et al. |
| 6,951,569 B2 | 10/2005 | Nohilly |
| 6,954,977 B2 | 10/2005 | Maguire et al. |
| 6,960,203 B2 | 11/2005 | Xiao et al. |
| 7,074,217 B2 | 7/2006 | Strul et al. |
| 7,083,614 B2 | 8/2006 | Fjield et al. |
| 7,087,052 B2 | 8/2006 | Sampson et al. |
| 7,108,696 B2 | 9/2006 | Daniel et al. |
| 7,118,590 B1 | 10/2006 | Cronin |
| 7,150,747 B1 | 12/2006 | Mcdonald et al. |
| 7,175,734 B2 | 2/2007 | Stewart et al. |
| 7,179,255 B2 | 2/2007 | Lettice et al. |
| 7,186,234 B2 | 3/2007 | Dahla et al. |
| 7,192,430 B2 | 3/2007 | Truckai et al. |
| 7,238,185 B2 | 7/2007 | Palanker et al. |
| 7,270,658 B2 | 9/2007 | Woloszko et al. |
| 7,276,063 B2 | 10/2007 | Davison et al. |
| 7,278,994 B2 | 10/2007 | Goble |
| 7,294,126 B2 | 11/2007 | Sampson et al. |
| 7,297,143 B2 | 11/2007 | Woloszko et al. |
| 7,326,201 B2 | 2/2008 | Fjield et al. |
| 7,331,957 B2 | 2/2008 | Woloszko et al. |
| RE40,156 E | 3/2008 | Sharps et al. |
| 7,371,231 B2 | 5/2008 | Rioux et al. |
| 7,371,235 B2 | 5/2008 | Thompson et al. |
| 7,381,208 B2 | 6/2008 | Van et al. |
| 7,387,628 B1 | 6/2008 | Behl et al. |
| 7,390,330 B2 | 6/2008 | Harp |
| 7,407,502 B2 | 8/2008 | Strul et al. |
| 7,419,500 B2 | 9/2008 | Marko et al. |
| 7,452,358 B2 | 11/2008 | Stern et al. |
| 7,462,178 B2 | 12/2008 | Woloszko et al. |
| 7,500,973 B2 | 3/2009 | Vancelette et al. |
| 7,512,445 B2 | 3/2009 | Truckai et al. |
| 7,530,979 B2 | 5/2009 | Ganz et al. |
| 7,549,987 B2 | 6/2009 | Shadduck |
| 7,556,628 B2 | 7/2009 | Utley et al. |
| 7,566,333 B2 | 7/2009 | Van et al. |
| 7,572,251 B1 | 8/2009 | Davison et al. |
| 7,604,633 B2 | 10/2009 | Truckai et al. |
| 7,625,368 B2 | 12/2009 | Schechter et al. |
| 7,674,259 B2 | 3/2010 | Shadduck |
| 7,678,106 B2 | 3/2010 | Lee |
| 7,708,733 B2 | 5/2010 | Sanders et al. |
| 7,717,909 B2 | 5/2010 | Strul et al. |
| 7,736,362 B2 | 6/2010 | Eberl et al. |
| 7,744,595 B2 | 6/2010 | Truckai et al. |
| 7,749,159 B2 | 7/2010 | Crowley et al. |
| 7,824,398 B2 | 11/2010 | Woloszko et al. |
| 7,824,405 B2 | 11/2010 | Woloszko et al. |
| 7,846,160 B2 | 12/2010 | Payne et al. |
| 7,879,034 B2 | 2/2011 | Woloszko et al. |
| 7,918,795 B2 | 4/2011 | Grossman |
| 7,985,188 B2 | 7/2011 | Felts et al. |
| 8,012,153 B2 | 9/2011 | Woloszko et al. |
| 8,197,476 B2 | 6/2012 | Truckai |
| 8,197,477 B2 | 6/2012 | Truckai |
| 8,323,280 B2 | 12/2012 | Germain et al. |
| 8,357,175 B2 | 1/2013 | Mark |
| 8,372,068 B2 | 2/2013 | Truckai |
| 8,382,753 B2 | 2/2013 | Truckai |
| 8,486,096 B2 | 7/2013 | Robertson et al. |
| 8,500,732 B2 | 8/2013 | Truckai et al. |
| 8,540,708 B2 | 9/2013 | Truckai et al. |
| 8,657,174 B2 | 2/2014 | Yates et al. |
| 8,690,873 B2 | 4/2014 | Truckai et al. |
| 8,702,702 B1 | 4/2014 | Edwards et al. |
| 8,821,486 B2 | 9/2014 | Toth et al. |
| 8,998,901 B2 | 4/2015 | Truckai et al. |
| 9,204,918 B2 | 12/2015 | Germain et al. |
| 9,277,954 B2 | 3/2016 | Germain et al. |
| 9,427,249 B2 | 8/2016 | Robertson et al. |
| 9,472,382 B2 | 10/2016 | Jacofsky |
| 9,510,897 B2 | 12/2016 | Truckai |
| 9,585,675 B1 | 3/2017 | Germain et al. |
| 9,592,085 B2 | 3/2017 | Germain et al. |
| 9,603,656 B1 | 3/2017 | Germain et al. |
| 9,649,125 B2 | 5/2017 | Truckai |
| 9,662,163 B2 | 5/2017 | Toth et al. |
| 9,901,394 B2 | 2/2018 | Shadduck et al. |
| 10,052,149 B2 | 8/2018 | Germain et al. |
| 10,213,246 B2 | 2/2019 | Toth et al. |
| 10,595,889 B2 | 3/2020 | Germain et al. |
| 2002/0058933 A1 | 5/2002 | Christopherson et al. |
| 2002/0062142 A1 | 5/2002 | Knowlton |
| 2002/0068934 A1 | 6/2002 | Edwards et al. |
| 2002/0082635 A1 | 6/2002 | Kammerer et al. |
| 2002/0183742 A1 | 12/2002 | Carmel et al. |
| 2003/0060813 A1 | 3/2003 | Loeb et al. |
| 2003/0065321 A1 | 4/2003 | Carmel et al. |
| 2003/0153905 A1 | 8/2003 | Edwards et al. |
| 2003/0171743 A1 | 9/2003 | Tasto et al. |
| 2003/0176816 A1 | 9/2003 | Maguire et al. |
| 2003/0236487 A1 | 12/2003 | Knowlton |
| 2004/0002702 A1 | 1/2004 | Xiao et al. |
| 2004/0010249 A1 | 1/2004 | Truckai et al. |
| 2004/0087936 A1 | 5/2004 | Stern et al. |
| 2004/0092980 A1 | 5/2004 | Cesarini et al. |
| 2004/0215180 A1 | 10/2004 | Starkebaum et al. |
| 2004/0215182 A1 | 10/2004 | Lee |
| 2004/0215296 A1 | 10/2004 | Ganz et al. |
| 2004/0230190 A1 | 11/2004 | Dahla et al. |
| 2005/0075630 A1 | 4/2005 | Truckai et al. |
| 2005/0165389 A1 | 7/2005 | Swain et al. |
| 2005/0182397 A1 | 8/2005 | Ryan |
| 2005/0192652 A1 | 9/2005 | Cioanta et al. |
| 2005/0240176 A1 | 10/2005 | Oral et al. |
| 2005/0251131 A1 | 11/2005 | Lesh |
| 2006/0009756 A1 | 1/2006 | Francischelli et al. |
| 2006/0052771 A1 | 3/2006 | Sartor et al. |
| 2006/0084158 A1 | 4/2006 | Viol |
| 2006/0084969 A1 | 4/2006 | Truckai et al. |
| 2006/0089637 A1 | 4/2006 | Werneth et al. |
| 2006/0189971 A1 | 8/2006 | Tasto et al. |
| 2006/0189976 A1 | 8/2006 | Karni et al. |
| 2006/0200040 A1 | 9/2006 | Weikel et al. |
| 2006/0224154 A1 | 10/2006 | Shadduck et al. |
| 2006/0259025 A1 | 11/2006 | Dahla |
| 2007/0021743 A1 | 1/2007 | Rioux et al. |
| 2007/0027447 A1 | 2/2007 | Theroux et al. |
| 2007/0083192 A1 | 4/2007 | Welch |
| 2007/0161981 A1 | 7/2007 | Sanders et al. |
| 2007/0213704 A1 | 9/2007 | Truckai et al. |
| 2007/0276430 A1 | 11/2007 | Lee et al. |
| 2007/0282323 A1 | 12/2007 | Woloszko et al. |
| 2007/0287996 A1 | 12/2007 | Rioux |
| 2007/0288075 A1 | 12/2007 | Dowlatshahi |
| 2007/0293853 A1 | 12/2007 | Truckai et al. |
| 2008/0058797 A1 | 3/2008 | Rioux |
| 2008/0097242 A1 | 4/2008 | Cai |
| 2008/0097425 A1 | 4/2008 | Truckai |
| 2008/0125765 A1 | 5/2008 | Berenshteyn et al. |
| 2008/0125770 A1 | 5/2008 | Kleyman |
| 2008/0154238 A1 | 6/2008 | Mcguckin |
| 2008/0183132 A1 | 7/2008 | Davies et al. |
| 2008/0208189 A1 | 8/2008 | Van et al. |
| 2008/0221567 A1 | 9/2008 | Sixto et al. |
| 2008/0249518 A1 | 10/2008 | Warnking et al. |
| 2008/0249533 A1 | 10/2008 | Godin |
| 2008/0249553 A1 | 10/2008 | Gruber et al. |
| 2008/0281317 A1 | 11/2008 | Gobel |
| 2009/0048593 A1 | 2/2009 | Ganz et al. |
| 2009/0054888 A1 | 2/2009 | Cronin |
| 2009/0054892 A1 | 2/2009 | Dicarlo et al. |
| 2009/0076494 A1 | 3/2009 | Azure |
| 2009/0105703 A1 | 4/2009 | Shadduck |
| 2009/0131927 A1 | 5/2009 | Kastelein et al. |
| 2009/0149846 A1 | 6/2009 | Hoey et al. |
| 2009/0163908 A1 | 6/2009 | Maclean et al. |
| 2009/0209956 A1 | 8/2009 | Marion |
| 2009/0270899 A1 | 10/2009 | Carusillo et al. |
| 2009/0306654 A1 | 12/2009 | Garbagnati |
| 2010/0004595 A1 | 1/2010 | Nguyen et al. |

(56) References Cited

U.S. PATENT DOCUMENTS

| | | | |
|---|---|---|---|
| 2010/0036372 A1 | 2/2010 | Truckai et al. | |
| 2010/0042095 A1 | 2/2010 | Bigley et al. | |
| 2010/0042097 A1 | 2/2010 | Taylor et al. | |
| 2010/0049190 A1 | 2/2010 | Long et al. | |
| 2010/0094289 A1 | 4/2010 | Taylor et al. | |
| 2010/0121319 A1 | 5/2010 | Chu et al. | |
| 2010/0125269 A1 | 5/2010 | Emmons et al. | |
| 2010/0137855 A1 | 6/2010 | Berjano et al. | |
| 2010/0137857 A1 | 6/2010 | Shroff et al. | |
| 2010/0152725 A1 | 6/2010 | Pearson et al. | |
| 2010/0185191 A1 | 7/2010 | Carr et al. | |
| 2010/0198214 A1 | 8/2010 | Layton, Jr. et al. | |
| 2010/0204688 A1 | 8/2010 | Hoey et al. | |
| 2010/0217245 A1 | 8/2010 | Prescott | |
| 2010/0217256 A1 | 8/2010 | Strul et al. | |
| 2010/0228239 A1 | 9/2010 | Freed | |
| 2010/0228245 A1 | 9/2010 | Sampson et al. | |
| 2010/0234867 A1 | 9/2010 | Himes | |
| 2010/0286680 A1 | 11/2010 | Kleyman | |
| 2010/0286688 A1 | 11/2010 | Hughett, Sr. et al. | |
| 2011/0004205 A1 | 1/2011 | Chu et al. | |
| 2011/0046513 A1 | 2/2011 | Hibner | |
| 2011/0060391 A1 | 3/2011 | Unetich et al. | |
| 2011/0112524 A1 | 5/2011 | Stern et al. | |
| 2011/0196401 A1 | 8/2011 | Robertson et al. | |
| 2011/0196403 A1 | 8/2011 | Robertson et al. | |
| 2012/0330292 A1 | 12/2012 | Shadduck et al. | |
| 2013/0018400 A1* | 1/2013 | Milton | A61B 90/98 606/167 |
| 2013/0085498 A1 | 4/2013 | Matusaitis et al. | |
| 2013/0090642 A1 | 4/2013 | Shadduck et al. | |
| 2013/0103021 A1 | 4/2013 | Germain et al. | |
| 2013/0103032 A1 | 4/2013 | Beaven | |
| 2013/0172870 A1 | 7/2013 | Germain et al. | |
| 2013/0231652 A1 | 9/2013 | Germain et al. | |
| 2013/0267937 A1 | 10/2013 | Shadduck et al. | |
| 2013/0296847 A1 | 11/2013 | Germain et al. | |
| 2013/0331833 A1 | 12/2013 | Bloom | |
| 2014/0100567 A1 | 4/2014 | Edwards et al. | |
| 2014/0114300 A1 | 4/2014 | Orczy-timko et al. | |
| 2014/0160015 A1 | 6/2014 | Ogawa et al. | |
| 2014/0276719 A1 | 9/2014 | Parihar | |
| 2014/0324065 A1 | 10/2014 | Bek et al. | |
| 2015/0053741 A1 | 2/2015 | Shelton, IV et al. | |
| 2015/0073341 A1 | 3/2015 | Salahieh et al. | |
| 2015/0088177 A1 | 3/2015 | Jezierski | |
| 2015/0119795 A1 | 4/2015 | Germain et al. | |
| 2015/0119916 A1 | 4/2015 | Dietz et al. | |
| 2015/0173827 A1 | 6/2015 | Bloom et al. | |
| 2015/0182281 A1 | 7/2015 | Truckai et al. | |
| 2016/0051307 A1 | 2/2016 | West, Jr. | |
| 2016/0066982 A1 | 3/2016 | Marczyk et al. | |
| 2016/0095615 A1 | 4/2016 | Orczy-timko et al. | |
| 2016/0113706 A1 | 4/2016 | Truckai et al. | |
| 2016/0157916 A1 | 6/2016 | Germain et al. | |
| 2016/0331443 A1 | 11/2016 | Phan et al. | |
| 2016/0346036 A1 | 12/2016 | Orczy-Timko et al. | |
| 2016/0346037 A1 | 12/2016 | Truckai et al. | |
| 2017/0202612 A1 | 7/2017 | Germain et al. | |
| 2017/0303990 A1 | 10/2017 | Benamou et al. | |
| 2018/0000534 A1 | 1/2018 | Germain et al. | |
| 2019/0021788 A1 | 1/2019 | Germain et al. | |

FOREIGN PATENT DOCUMENTS

| | | |
|---|---|---|
| CN | 101015474 A | 8/2007 |
| CN | 101198288 A | 6/2008 |
| CN | 105658152 A | 6/2016 |
| CN | 109561899 A | 4/2019 |
| EP | 1236440 A1 | 9/2002 |
| EP | 1595507 A2 | 11/2005 |
| EP | 2349044 A1 | 8/2011 |
| EP | 2493407 A1 | 9/2012 |
| EP | 2772206 A2 | 9/2014 |
| EP | 2981222 A1 | 2/2016 |
| EP | 3445258 A1 | 2/2019 |
| JP | 2005501597 A | 1/2005 |
| JP | 2019514481 A | 6/2019 |
| WO | WO-9624296 A1 | 8/1996 |
| WO | WO-0053112 A2 | 9/2000 |
| WO | WO-2005122938 A1 | 12/2005 |
| WO | WO-2006001455 A1 | 1/2006 |
| WO | WO-2008083407 A1 | 7/2008 |
| WO | WO-2010048007 A1 | 4/2010 |
| WO | WO-2011053599 A1 | 5/2011 |
| WO | WO-2011060301 A1 | 5/2011 |
| WO | WO-2013009252 A2 | 1/2013 |
| WO | WO-2013067417 A1 | 5/2013 |
| WO | WO-2014165715 A1 | 10/2014 |
| WO | WO-2015026644 A1 | 2/2015 |
| WO | WO-2016171963 A1 | 10/2016 |
| WO | WO-2016175980 A1 | 11/2016 |
| WO | WO-2017127760 A1 | 7/2017 |
| WO | WO-2017185097 A1 | 10/2017 |
| WO | WO-2018005382 A1 | 1/2018 |
| WO | WO-2017185097 A8 | 11/2018 |

OTHER PUBLICATIONS

"U.S. Appl. No. 12/541,043, Non Final Office Action dated Mar. 12, 2012", 12 pgs.

"U.S. Appl. No. 12/541,043, Notice of Allowance dated Nov. 15, 2012".

"U.S. Appl. No. 12/541,050, Final Office Action dated Sep. 28, 2012", 6 pgs.

"U.S. Appl. No. 12/541,050, Non Final Office Action dated Mar. 12, 2012", 9 pgs.

"U.S. Appl. No. 12/541,050, Notice of Allowance dated Nov. 15, 2012".

"U.S. Appl. No. 12/605,546, Final Office Action dated Jan. 28, 2013", 7 pgs.

"U.S. Appl. No. 12/605,546, Non Final Office Action dated Jun. 18, 2012", 22 pgs.

"U.S. Appl. No. 12/605,546, Notice of Allowance dated Mar. 29, 2013", 6 pgs.

"U.S. Appl. No. 12/605,929, Non Final Office Action dated Sep. 28, 2012", 12 pgs.

"U.S. Appl. No. 12/605,929, Notice of Allowance dated May 24, 2013", 8 pgs.

"U.S. Appl. No. 12/944,466, Notice of Allowance dated May 9, 2014", 9 pgs.

"U.S. Appl. No. 13/236,471, Final Office Action dated Jul. 5, 2016", 14 pgs.

"U.S. Appl. No. 13/236,471, Non Final Office Action dated Sep. 24, 2015", 15 pgs.

"U.S. Appl. No. 13/236,471, Non Final Office Action dated Dec. 4, 2014", 16 pgs.

"U.S. Appl. No. 13/236,471, Notice of Allowance dated Jan. 27, 2017", 7 pgs.

"U.S. Appl. No. 13/281,805, Final Office Action dated Mar. 31, 2016", 9 pgs.

"U.S. Appl. No. 13/281,805, Final Office Action dated Dec. 16, 2014", 11 pgs.

"U.S. Appl. No. 13/281,805, Non Final Office Action dated Jul. 23, 2015", 9 pgs.

"U.S. Appl. No. 13/281,805, Non Final Office Action dated Sep. 22, 2014", 11 pgs.

"U.S. Appl. No. 13/281,805, Notice of Allowance dated Aug. 2, 2016", 11 pgs.

"U.S. Appl. No. 13/281,846, Non Final Office Action dated Dec. 6, 2011", 11 pgs.

"U.S. Appl. No. 13/281,846, Notice of Allowance dated Mar. 5, 2012", 7 pgs.

"U.S. Appl. No. 13/281,856, Non Final Office Action dated Dec. 22, 2011", 8 pgs.

"U.S. Appl. No. 13/281,856, Notice of Allowance dated Mar. 5, 2012", 7 pgs.

(56) References Cited

OTHER PUBLICATIONS

"U.S. Appl. No. 13/857,068, Final Office Action dated Feb. 4, 2016", 8 pgs.
"U.S. Appl. No. 13/857,068, Final Office Action dated Apr. 5, 2017", 12 pgs.
"U.S. Appl. No. 13/857,068, Non Final Office Action dated Jun. 5, 2015", 8 pgs.
"U.S. Appl. No. 13/857,068, Non Final Office Action dated Sep. 7, 2016", 11 pgs.
"U.S. Appl. No. 13/857,068, Non Final Office Action dated Oct. 9, 2014", 9 pgs.
"U.S. Appl. No. 13/857,068, Notice of Allowance dated Dec. 14, 2017", 7 pgs.
"U.S. Appl. No. 13/938,032, Non Final Office Action dated Nov. 6, 2013", 7 pgs.
"U.S. Appl. No. 13/938,032, Notice of Allowance dated Jan. 9, 2014", 5 pgs.
"U.S. Appl. No. 13/975,139, Final Office Action dated Oct. 24, 2014", 6 pgs.
"U.S. Appl. No. 13/975,139, Non Final Office Action dated Apr. 24, 2014", 9 pgs.
"U.S. Appl. No. 13/975,139, Notice of Allowance dated Feb. 25, 2015", 2 pgs.
"U.S. Appl. No. 13/975,139, Notice of Allowance dated Dec. 2, 2014", 6 pgs.
"U.S. Appl. No. 14/341,121, Final Office Action dated Jun. 28, 2018", 7 pgs.
"U.S. Appl. No. 14/341,121, Non Final Office Action dated Nov. 27, 2017", 10 pgs.
"U.S. Appl. No. 14/341,121, Notice of Allowance dated Oct. 19, 2018", 7 pgs.
"U.S. Appl. No. 14/341,121, Notice of Allowance dated Nov. 15, 2018", 4 pgs.
"U.S. Appl. No. 14/508,856, Non Final Office Action dated Jun. 29, 2016", 10 pgs.
"U.S. Appl. No. 14/508,856, Notice of Allowance dated Jan. 27, 2017", 10 pgs.
"U.S. Appl. No. 14/657,684, Final Office Action dated Apr. 18, 2017", 9 pgs.
"U.S. Appl. No. 14/657,684, Final Office Action dated Apr. 22, 2016", 9 pgs.
"U.S. Appl. No. 14/657,684, Non Final Office Action dated May 22, 2015", 7 pgs.
"U.S. Appl. No. 14/657,684, Non Final Office Action dated Jul. 12, 2018", 8 pgs.
"U.S. Appl. No. 14/657,684, Non Final Office Action dated Nov. 2, 2016", 9 pgs.
"U.S. Appl. No. 14/864,379, Final Office Action dated Jun. 15, 2018", 16 pgs.
"U.S. Appl. No. 14/864,379, Non Final Office Action dated Dec. 5, 2017", 12 pgs.
"U.S. Appl. No. 15/008,341, Non Final Office Action dated Jan. 2, 2019", 11 pgs.
"U.S. Appl. No. 15/091,402, Final Office Action dated Mar. 9, 2017", 16 pgs.
"U.S. Appl. No. 15/091,402, Final Office Action dated Mar. 14, 2018", 12 pgs.
"U.S. Appl. No. 15/091,402, Non Final Office Action dated Jul. 28, 2017", 13 pgs.
"U.S. Appl. No. 15/091,402, Non Final Office Action dated Sep. 30, 2016", 22 pgs.
"U.S. Appl. No. 15/091,402, Notice of Allowance dated Feb. 3, 2020", 6 pgs.
"U.S. Appl. No. 15/410,723, Final Office Action dated May 9, 2017", 12 pgs.
"U.S. Appl. No. 15/410,723, Non Final Office Action dated Mar. 14, 2017", 12 pgs.
"U.S. Appl. No. 15/410,723, Notice of Allowance dated Apr. 24, 2018", 8 pgs.
"U.S. Appl. No. 15/488,270, Non Final Office Action dated Feb. 19, 2019", 7 pgs.
"U.S. Appl. No. 15/495,620, Final Office Action dated May 28, 2021", 11 pgs.
"U.S. Appl. No. 15/495,620, Non Final Office Action dated Nov. 27, 2020", 13 pgs.
"U.S. Appl. No. 15/495,620, Notice of Allowance dated Oct. 15, 2021", 11 pgs.
"U.S. Appl. No. 15/495,620, Response filed Feb. 18, 2021 to Non Final Office Action dated Nov. 27, 2020", 10 pgs.
"U.S. Appl. No. 15/495,620, Response filed Jul. 26, 2021 to Final Office Action dated May 28, 2021", 8 pgs.
"U.S. Appl. No. 15/495,620, Response filed Jul. 29, 20 to Restriction Requirement dated Jun. 25, 2020", 1 pg.
"U.S. Appl. No. 15/495,620, Restriction Requirement dated Jun. 25, 2020", 7 pgs.
"U.S. Appl. No. 15/583,712, Non Final Office Action dated Nov. 1, 2018", 9 pgs.
"U.S. Appl. No. 15/633,372, Final Office Action dated Dec. 26, 2019", 21 pgs.
"U.S. Appl. No. 15/633,372, Non Final Office Action dated May 2, 2019", 24 pgs.
"Chinese Application Serial No. 201780038215.4, Notification to Make Rectification dated Jan. 8, 2019", W/ English Translation, 2 pgs.
"Chinese Application Serial No. 201780038215.4, Office Action dated Nov. 17, 2020", w/o English Translation, 11 pgs.
"Co-pending U.S. Appl. No. 15/271,184, filed Sep. 20, 2016".
"Co-pending U.S. Appl. No. 15/421,264, filed Jan. 31, 2017".
"Co-pending U.S. Appl. No. 15/454,342, filed Mar. 9, 2017".
"Co-pending U.S. Appl. No. 15/483,940, filed Apr. 10, 2017".
"European Application Serial No. 09822443, Extended European Search Report dated Apr. 16, 2013", 7 pgs.
"European Application Serial No. 10827399, Extended European Search Report datd Jul. 10, 2013", 6 pgs.
"European Application Serial No. 16786901.5, Extended European Search Report dated Nov. 19, 2018", 7 pgs.
"European Application Serial No. 17742070.0, Extended European Search Report dated May 23, 2019", 7 pgs.
"European Application Serial No. 17786807.2, Extended European Search Report dated Nov. 4, 2019", 7 pgs.
"European Application Serial No. 17786807.2, Response filed May 26, 2020 to Extended European Search Report dated Nov. 4, 2019", 47 pgs.
"European Application Serial No. 17821026.6, Extended European Search Report dated Mar. 31, 2020", 9 pgs.
"International Application Serial No. PCT/US2009/060703, International Search Report dated Dec. 10, 2009", 2 pgs.
"International Application Serial No. PCT/US2009/060703, Written Opinion dated Dec. 10, 2009", 6 pgs.
"International Application Serial No. PCT/US2010/054150, International Search Report dated Dec. 14, 2010", 2 pgs.
"International Application Serial No. PCT/US2010/054150, Written Opinion dated Dec. 14, 2010", 11 pgs.
"International Application Serial No. PCT/US2014/032895, International Search Report dated Sep. 10, 2014", 2 pgs.
"International Application Serial No. PCT/US2016/025509, International Search Report dated Jul. 6, 2016", 2 pgs.
"International Application Serial No. PCT/US2017/014456, International Search Report dated May 31, 2017", 4 pgs.
"International Application Serial No. PCT/US2017/014456, Written Opinion dated May 31, 2017", 7 pgs.
"International Application Serial No. PCT/US2017/029201, International Preliminary Report on Patentability dated Nov. 1, 2018", 8 pgs.
"International Application Serial No. PCT/US2017/029201, International Search Report dated Jul. 7, 2017", 2 pgs.
"International Application Serial No. PCT/US2017/029201, Written Opinion dated Jul. 7, 2017", 6 pgs.
"International Application Serial No. PCT/US2017/039326, International Search Report dated Nov. 3, 2017", 4 pgs.
"International Application Serial No. PCT/US2017/039326, Written Opinion dated Nov. 3, 2017", 10 pgs.

(56) References Cited

OTHER PUBLICATIONS

Allen-Bradley, "AC Braking Basics", Web article, Rockwell Automation, Rockwell International Corporation, [Online]. Retrieved from the Internet: <http://literature.rockwellautomation.com/idc/groups/literature/documents/wp/drives-wp004_-enp.pdf>, (Feb. 2001), 4 pgs.

Allen-Bradley, "What Is Regeneration? Braking / Regeneration Manual: Regeneration Overview", Revision 1.0. Rockwell Automation, [Online]. Retrieved from the Internet: <https://www.ab.com/supportlabdrives/documentation/techpapers/RegenOverview01.pdf> Accessed Apr. 24, 2017, 6 pgs.

Volpato, et al., "Application of Zirconia in Dentistry: Biological, Mechanical and Optical Considerations.", Advances in ceramics—electric and magnetic ceramics, bioceramics, ceramics and environment, (Sep. 2011), 397-420.

\* cited by examiner

ARTHROSCOPIC DEVICES AND METHODS

CROSS-REFERENCE TO RELATED APPLICATIONS

This application claims the benefit of provisional application No. 62/326,544, filed on Apr. 22, 2016, the full disclosure of which is incorporated herein by reference.

BACKGROUND OF THE INVENTION

1. Field of the Invention

This invention relates to surgical systems and their use, such as an arthroscopic and other endoscopic tissue cutting and removal system wherein a motor-driven electrosurgical device is provided for cutting and removing bone or soft tissue from a joint or other site. More specifically, this invention relates to systems and methods for device identification, monitoring, and control, such as controlled operational stopping and starting of motor-driven components in default positions.

2. Description of the Background Art

In arthroscopic, endoscopic, and other surgical procedures including subacromial decompression, anterior cruciate ligament reconstruction involving notchplasty, and arthroscopic resection of the acromioclavicular joint, there is a need for cutting and removal of bone and soft tissue. Currently, surgeons use arthroscopic shavers and burrs having rotational cutting surfaces to remove hard tissue in such procedures.

To promote efficiency, endoscopic tool systems including a reusable handpiece and a selection of interchangeable tool probes having different working ends have been proposed. Such working ends may each have two or more functionalities, such as soft tissue removal and hard tissue resection, so such tools systems can provide dozens of specific functionalities, providing great flexibility.

While a significant advantage, the need for one tool system to accommodate such flexibility is a challenge. In particular, it is necessary that the handpiece and control unit for the system be provided with correct information on the identity of the tool probe that has been attached as well as the operational parameters of the tool probe during use.

It is therefore an object of the present invention to provide improved surgical systems and methods for their use, such as improved arthroscopic tissue cutting and removal system wherein a motor-driven electrosurgical device is provided for cutting and removing bone or soft tissue from a joint or other site. It is a further object invention to provide improved systems and methods for device identification, monitoring, and control, such as controlled operational stopping and starting of motor-driven components in default positions. At least some of these objectives will be met by the inventions described herein.

SUMMARY OF THE INVENTION

The present invention provides improved apparatus and methods for identifying and controlling working components, such as motor-driven and other powered components, of surgical systems, particularly for arthroscopic and other surgical systems including (1) handpieces having motor drive units and (2) probes which are selectively and removably attached to the handpieces. In exemplary embodiments, the present invention provides methods and systems which rely on magnets and magnetic sensors for providing information to system controllers both in a static mode, where a endoscopic or other tool is not being driven, and in a dynamic mode, where the tool is being driven by the motor drive. In particular embodiments, the magnets are permanent magnets having North poles and South poles, where the magnets are typically mounted on or otherwise attached or coupled to components of a detachable probe forming part of an arthroscopic system, and the sensors are Hall sensors which are in the handpiece of the arthroscopic system. By using multiple magnets and multiple sensors, different types of information can be provided to the system controller, such as identification of the tool in the detachable probe, operating characteristics of the probe, system calibration information, and the like. While the exemplary embodiments of present invention typically rely on magnetic sensors, static and dynamic data acquisition from the tool probe to the associated controller and be accomplished with other sensors as well, such as optical sensors which are able to read information in both a static mode and in a dynamic mode.

In a first aspect of the present invention, an arthroscopic system comprises a handpiece and a probe. The handpiece includes a motor drive, and the probe has a proximal hub and an elongate shaft which extends about a longitudinal axis to a working end of the probe. The hub is configured for detachably coupling to the handpiece, and the motor drive is configured to couple to a rotating drive coupling in the hub when the hub is coupled to the handpiece. A first magnetic component is carried by the hub, and a second magnetic component is coupled to rotate with the rotating drive coupling.

In specific aspects, the hub may be configured for detachable coupling to the handpiece in opposing rotational orientations, such as an orientation where a working end of the probe is facing upwardly and a second orientation where the working end of the probe is facing downwardly relative to the handpiece. In such embodiments, the first magnetic component may comprise first and second independent magnets, typically permanent magnets have North poles and South poles, disposed in or on opposing sides of the hub and spaced outwardly from the longitudinal axis. The first and second independent magnets of the first magnetic component will typically have a "polar orientation," for example the North poles will be oriented in opposite directions relative to said axis. Typically, though not necessarily, the first and second independent magnets may have similar magnetic field strengths. In such embodiments, the handpiece may further comprise a first sensor configured for "statically" sensing a magnetic field of the first or second independent magnets when located adjacent the first sensor. By "statically" sensing, it is meant that the magnets do not need to be moving relative to the sensor. The sensor will thus be able to generate a signal indicating whether the working end is in its upward-facing orientation or its downward-facing orientation. The first sensor may be further configured for generating a probe identification signal based on the magnetic field strength (or other magnetic characteristic) which correlates a probe type with different magnetic field strengths, typically by using a look-up table maintained in an associated controller.

In still other embodiments, the second magnetic component comprises third and fourth independent magnets disposed in or on opposing sides of the rotating drive coupling. The third and fourth independent magnets of the second magnetic component will typically have North poles in opposing orientations relative to said axis, usually in a manner similar to the first and second independent magnets. The handpiece will further comprise a second sensor configured for sensing a magnetic field of the third or fourth independent magnets as the magnet comes into proximity to the second sensor. In this way, the second sensor can dynamically sense and generate a signal indicating a rotational parameter of the rotating drive coupling. For example, the rotational parameter may comprise a rotational position of the drive coupling. Alternatively or additionally, the rotational parameter may comprise a rotational speed of the drive coupling based on the rotational positioning over a time interval.

These arthroscopic and other surgical systems may be further configured for determining orientation of the motor-driven component so that the working end can be stopped in a desired position. For example, the second magnetic component carried by the drive coupling may be in a fixed predetermined rotational relationship to a motor-driven component in the working end. In this way, a rotational positioning of the component in the working end van be controlled based on the rotational position of the drive coupling.

Such systems of the present invention may further comprise a controller configured to receive the signals generated by the sensors and provide monitoring and control of the endoscopic or other surgical tool based on the received signals. For example, by receiving signals generated by the first sensor within the hub, at least one of probe-orientation and probe identification can be determined. Similarly, by receiving signals generated by the second sensor within the hub, the controller may be configured to monitor and/or control the motor speed and other operational characteristics.

In a second aspect of the present invention, a method for performing an arthroscopic procedure comprises providing a system including a handpiece with a sensor. The system further comprises a probe having a proximal hub, a longitudinal axis, and a working end. The hub typically carries first and second magnets having North and South poles. The hub is selectively coupled to the handpiece with the working end of the probe in either an upward orientation or a downward orientation. The first magnet is located proximately to sensor when the working end is in the upward orientation, and the second magnet is located proximately to sensor when the working end is in the down orientation. In this way, an upward orientation or a downward orientation of the working end can be determined based on whether a North pole or a South pole of the magnet is proximate to the sensor. Such "orientational" information is used for a variety of purposes, including selecting a controller algorithm for operating the probe based on the identified orientation of the working end.

In a third aspect of the present invention, an arthroscopic or other surgical method comprises providing a system including a handpiece with a sensor. The system further comprises a probe with a proximal hub, a longitudinal axis, and a working end. The hub will carry first and second magnets of similar strengths and having North and South poles. The hub is coupled to the handpiece, and a magnetic strength of either (or both) of the magnets is sensed using a sensor in the handpiece to identify the probe type based on the sensed magnetic strength. Identification of the probe type is useful for a variety of purposes, including allowing selection of a control algorithm (to be used by a controller coupled to probe and sensors) to control the working end of the tool based on the identified probe type.

In a fourth aspect, an arthroscopic or other surgical procedure comprises providing a system including a handpiece with a motor drive. The system further comprises a probe having a proximal hub, a longitudinal axis, a rotating drive coupling, and a working end. The rotating drive coupling typically carries first and second magnets having North and South poles where each pole is positioned in a different orientation relative to the axis. The hub is attached to the handpiece to couple the motor drive to the rotating drive coupling in the hub. The rotating drive coupling actuates a motor-driven or other component in the working end, e.g. the motor drive may be activated to rotate the drive coupling and actuate the motor-driven component. A varying magnetic parameter is sensed with a sensor in the handpiece as the drive coupling rotates in order to generate sensor signals. A rotational position of the drive coupling can thus be determined, and the corresponding positions of the motor-driven component calculated using a positioning algorithm responsive to the sensor signals. The motor drive can be selectively deactivated at a desired rotational position based on the positional information which has been thus determined. After deactivating the motor drive, the system can dynamically brake the motor drive to thereby stop rotation of the drive coupling and stop movement of the motor-driven component in a selective stop position in a highly accurate manner.

In a fifth aspect of the present invention, an arthroscopic procedure comprises providing a system including a handpiece with a motor drive. The system further comprises a probe with a proximal hub and an elongate shaft extending about an axis to a working end. The hub is configured for detachable coupling to the handpiece, and the motor drive is configured to couple to a rotating drive coupling in the hub. The drive coupling, in turn, carries first and second magnets with North and South poles positioned in different orientations relative to the axis. The hub is coupled to the handpiece, and the motor drive is activated to rotate the drive coupling and magnets through an arc of at least 180°. A varying strength of each magnet is then sensed with a sensor in the handpiece as the drive coupling rotates. A rotational position of the drive coupling responsive to the varying strength of each magnet can be calibrated in order to increase accuracy in subsequent calculation of the sensed strengths of the magnets.

In a sixth aspect of the present invention, an arthroscopic procedure comprises providing a handpiece with a motor drive. The system further comprises a probe having a proximal hub and an elongate shaft extending about a longitudinal axis to a working end having a motor-driven component. The motor-driven component includes a radio frequency (RF) electrode, and a hub is configured for detachable coupling to the handpiece. The motor drive is configured to couple to a rotating drive in the coupling of the hub, and the rotating drive coupling is configured to carry first and second magnets with North and South poles positioned in different orientations relative to the axis. The hub is coupled to the handpiece, and the drive coupling and motor-driven component are positioned in a selected stop position. The RF electrode is typically exposed in the selected stop position and can be introduced to a target site to engage or interface with tissue. RF current is then delivered to the RF electrode, and a positioning algorithm responsive to sensor signals continuously monitors the rotational position of the drive coupling and the corresponding position of the motor-driven component and the RF electrode while RF current is being delivered. Such position monitoring is useful because it allows the positioning algorithm to sense a rotation or rotational deviation greater than a predetermined amount, in which case the delivery of RF current to the RF electrode can be terminated. Additionally or alternatively, the positioning algorithm can further activate or adjust the motor drive to return the RF electrode back to a selected or desired stop position.

In a seventh aspect, an arthroscopic procedure comprises providing a handpiece with a motor drive and a probe with a proximal hub. An elongate shaft of the hub extends about an axis to a working end, and a motor driven component in the working end includes an RF electrode. The hub is configured for detachably coupling to the handpiece, and the motor drive is configured to couple to a rotating drive coupling in the hub. The rotating drive carries first and second magnets with North and South poles having different orientations relative to the axis. The hub is coupled to the handpiece, and the drive coupling and motor-driven component may be positioned in a selected stop position. The RF electrode may be engaged against a target issue surface or interface, and an RF current may be delivered to the RF electrode. Using a positioning algorithm responsive to sensor signals indicating a rotational position of the drive coupling, the RF electrode can be oscillated in the range from 20 Hz to 2000 Hz. Often, oscillation of the RF electrode at a rate ranging from 40 Hz to 400 Hz.

In an eighth aspect, the present invention comprises a method for providing information from a surgical probe to a controller. A hub of the probe is attached to a handpiece connected to the controller. The hub carries indicia, and a first set of data obtained from reading the first set of indicia on the hub may be read using a first sensor on the handpiece, where the first set of data can then be sent to the controller. A second set of indicia on the hub is also read using a second sensor on the handpiece, and a second set of data obtained from the second reading may also be sent to the controller. The first set of data includes at least one of probe identification information and probe orientation information, and the second set of data includes at least probe operational information.

In specific embodiments, the first and/or second set of indicia may comprise magnets, as taught in any of previously described embodiments. In alternative embodiments, however, the first and/or second sets of indicia may comprise optical encoding or any other type of data encoding that can be read using sensors in the handpiece. For example, the first set of indicia may comprise optical encoding including a scannable code on a stationary component of the hub, such as a housing. The first set of indicia incorporates said at least one of probe identification information and probe orientation information and can be read when the code is static relative to the handpiece, typically using a stationary optical scanner, such as a bar or 3D code reader. In other examples, the second set of indicia may comprise optical encoding configured to be read by a scannable code reader, e.g., markings on a rotatable component of the hub, wherein at least the probe operational information is configured to read from the markings as the rotatable component dynamically rotates. For example, the markings may be read by an optical counter that can determine a rotation speed, such as revolutions per minute (RPM).

In some embodiments, the probe will include a rotary-to-linear converter for receiving rotary motion from the rotary drive coupling in the hub and converting the rotary motion to linear motion, typically reciprocating motion, e.g., for driving a reciprocating electrode, a reciprocating cutting blade, pivoting a jaw member (where the reciprocating motion can be further converted into pivoting motion), and the like, as described elsewhere herein. In all such cases, a magnet or other detectable element can be placed on the reciprocating or pivoting element in addition to, or in some cases in place of, the magnet or other detectable element that is on or otherwise coupled to the rotary drive coupling in the hub. In such cases, a magnetic or other sensor in the handpiece will be located to detect linear motion, typically to determine reciprocation rate, reciprocation distance, or other performance parameter.

BRIEF DESCRIPTION OF THE DRAWINGS

Various embodiments of the present invention will now be discussed with reference to the appended drawings. It should be appreciated that the drawings depict only typical embodiments of the invention and are therefore not to be considered limiting in scope.

DETAILED DESCRIPTION OF THE INVENTION

The present invention relates to bone cutting and tissue removal devices and related methods of use. Several variations of the invention will now be described to provide an overall understanding of the principles of the form, function and methods of use of the devices disclosed herein. In general, the present disclosure provides for variations of arthroscopic tools adapted for cutting bone, soft tissue, meniscal tissue, and for RF ablation and coagulation. The arthroscopic tools are typically disposable and are configured for detachable coupling to a non-disposable handpiece that carries a motor drive component. This description of the general principles of this invention is not meant to limit the inventive concepts in the appended claims.

Figure 1:
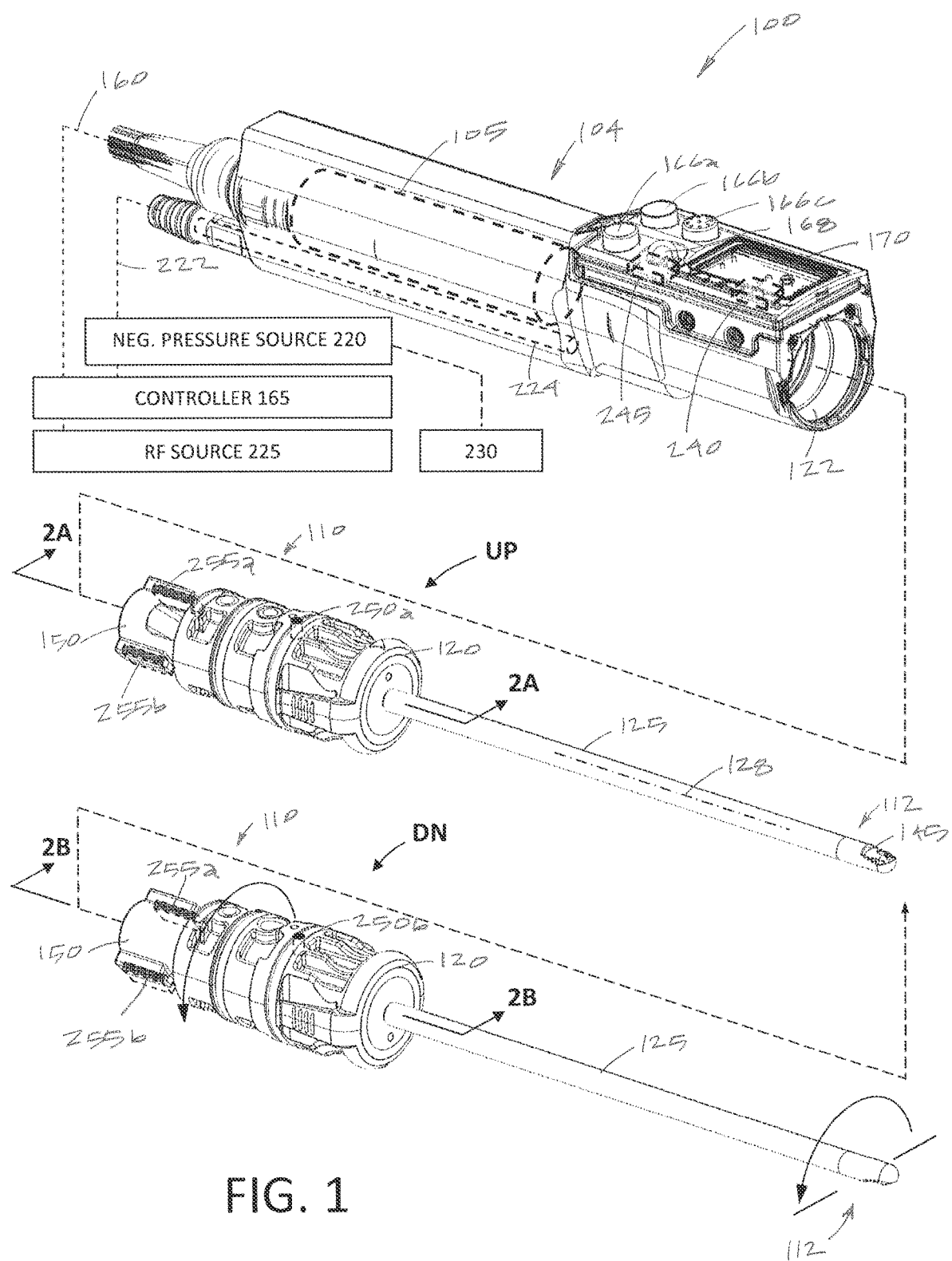
FIG. 1 is a perspective view of an arthroscopic cutting system that includes reusable handpiece with a motor drive and a detachable single-use cutting probe, wherein the cutting probe is shown in two orientations as it may be coupled to the handpiece with the probe and working end in upward orientation or a downward orientation relative to the handpiece, and wherein the handpiece includes an LCD screen for displaying operating parameters of system during use together with control actuators on the handpiece.

In one variation shown in FIG. 1, the arthroscopic system 100 of the present invention provides a handpiece 104 with motor drive 105 and a disposable shaver assembly or probe 110 with a proximal hub 120 that can be received by receiver or bore 122 in the handpiece 104. In one aspect, the probe 110 has a working end 112 that carries a high-speed rotating cutter that is configured for use in many arthroscopic surgical applications, including but not limited to treating bone in shoulders, knees, hips, wrists, ankles and the spine.

Figure 2A:
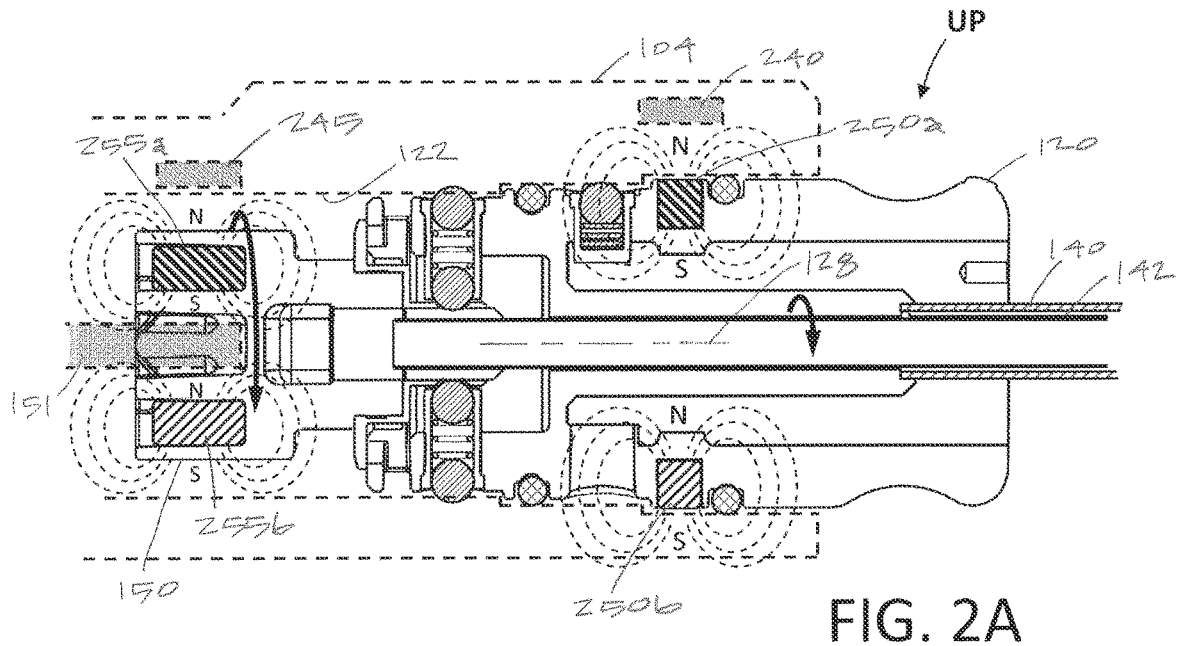
FIG. 2A is an enlarged longitudinal sectional view of the hub of the probe of FIG. 1 taken along line 2A-2A of FIG. 1 with the hub and probe in an upward orientation relative to the handpiece, further showing Hall effect sensors carried by the handpiece and a plurality of magnets carried by the probe hub for device identification, for probe orientation and determining the position of motor driven components of the probe relative to the handpiece.
Figure 3A:
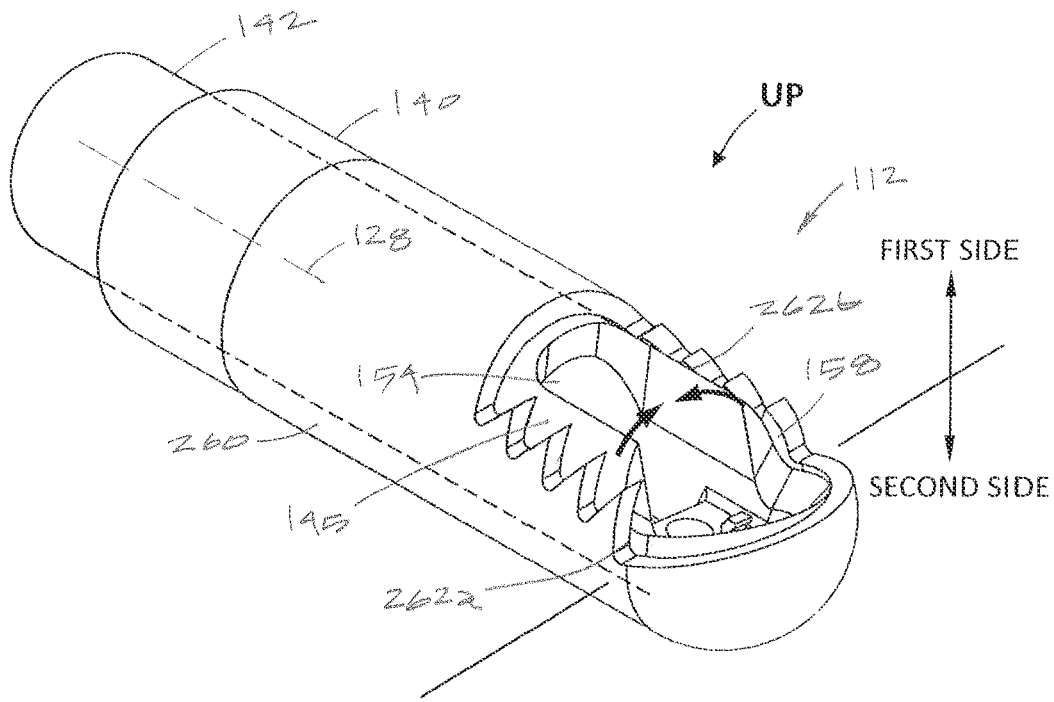
FIG. 3A is an enlarged perspective view of the working end of the probe of FIG. 1 in an upward orientation with the rotatable cutting member in a first position relative to the outer sleeve wherein the window in the cutting member is aligned with the window of the outer sleeve.
Figure 3B:
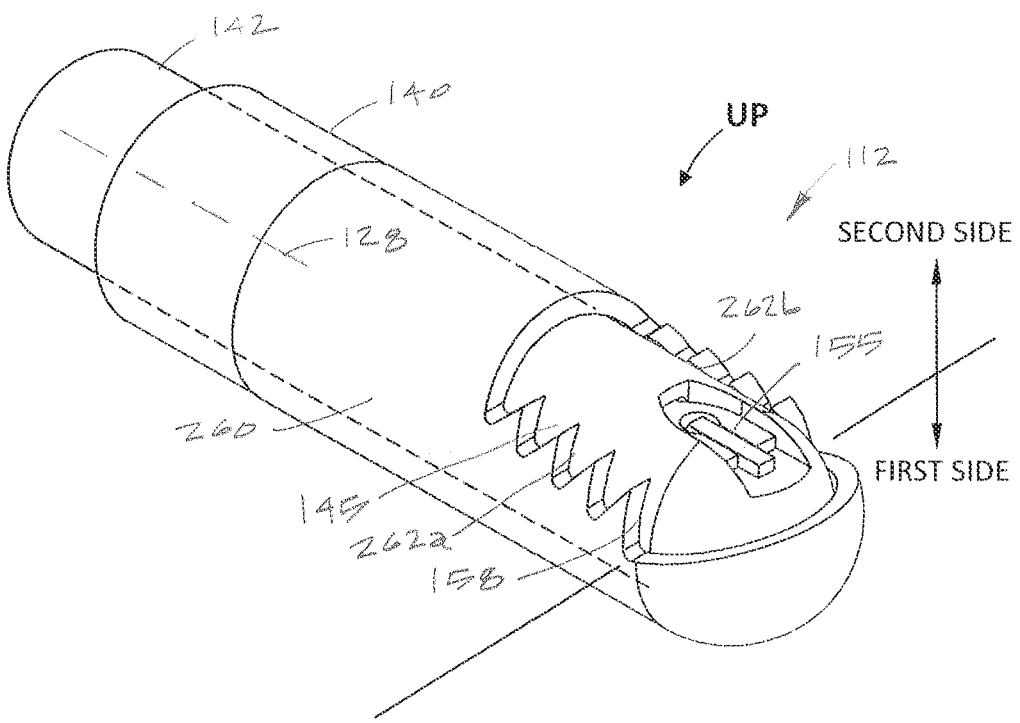
FIG. 3B is a perspective view of the working end of FIG. 1 in an upward orientation with the rotatable cutting member in a second position relative to the outer sleeve wherein the electrode carried by the cutting member is aligned with a centerline of the window of the outer sleeve.

In FIGS. 1, 2A and 3A, it can be seen that probe 110 has a shaft 125 extending along longitudinal axis 128 that comprises an outer sleeve 140 and an inner sleeve 142 rotatably disposed therein with the inner sleeve 142 carrying a distal ceramic cutting member 145 (FIG. 3A). The shaft 125 extends from the proximal hub 120 wherein the outer sleeve 140 is coupled in a fixed manner to the hub 120 which can be an injection molded plastic, for example, with the outer sleeve 140 insert molded therein. The inner sleeve 142 is coupled drive coupling 150 that is configured for coupling to the rotating motor shaft 151 of motor drive unit 105. More in particular, the rotatable cutting member 145 that is fabricated of a ceramic material with sharp cutting edges on opposing sides 152a and 152b of window 154 therein for cutting soft tissue. The motor drive 105 is operatively coupled to the ceramic cutter to rotate the cutting member at speeds ranging from 1,000 rpm to 20,000 rpm. In FIG. 3B, it can be seen that cutting member 145 also carries an RF electrode 155 in a surface opposing the window 154. The cutting member 145 rotates and shears tissue in the toothed opening or window 158 in the outer sleeve 140 (FIG. 3A). A probe of the type shown in FIG. 1 is described in more detail in co-pending and commonly owned patent application Ser. No. 15/421,264 filed Jan. 31, 2017 titled ARTHROSCOPIC DEVICES AND METHODS which is incorporated herein in its entirety by this reference.

As can be seen in FIG. 1, the probe 110 is shown in two orientations for detachable coupling to the handpiece 104. More particularly, the hub 120 can be coupled to the handpiece 104 in an upward orientation indicated at UP and a downward orientation indicated at DN where the orientations are 180° opposed from one another. It can be understood that the upward and downward orientations are necessary to orient the working end 112 either upward or downward relative to the handpiece 104 to allow the physician to interface the cutting member 145 with targeted tissue in all directions without having to manipulate the handpiece in 360° to access tissue.

In FIG. 1, it can be seen that the handle 104 is operatively coupled by electrical cable 160 to a controller 165 which controls the motor drive unit 105. Actuator buttons 166a, 166b or 166c on the handle 104 can be used to select operating modes, such as various rotational modes for the ceramic cutting member 145. In one variation, a joystick 168 can be moved forward and backward to adjust the rotational speed of the ceramic cutting member 145. The rotational speed of the cutter can continuously adjustable, or can be adjusted in increments up to 20,000 rpm. An LCD screen 170 is provided in the handpiece for displaying operating parameters, such as cutting member RPM, mode of operation, etc.

Figure 4:
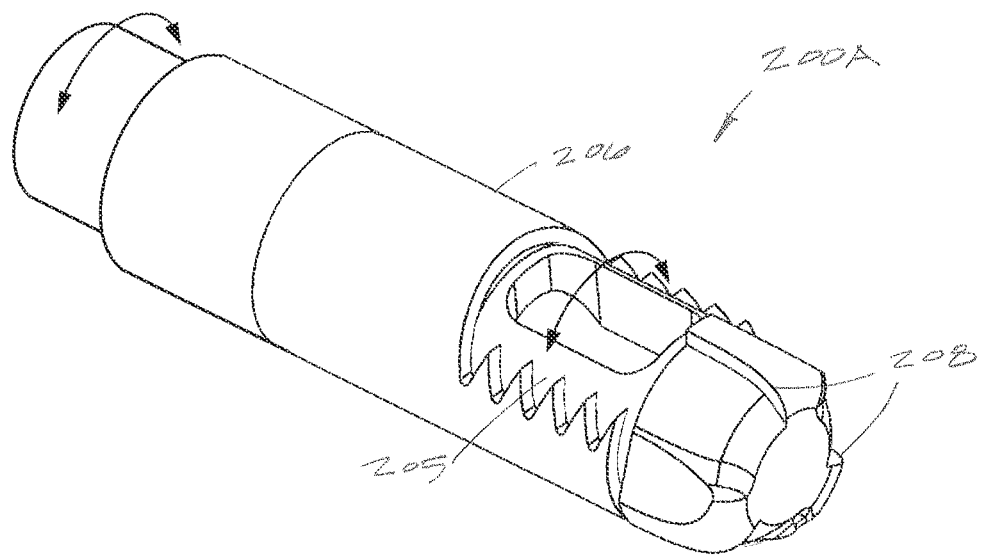
FIG. 4 is a perspective view of a working end of a variation of a probe that may be detachably coupled to the handpiece of FIG. 1, wherein the working end includes a bone burr extending distally from the outer sleeve.
Figure 5:
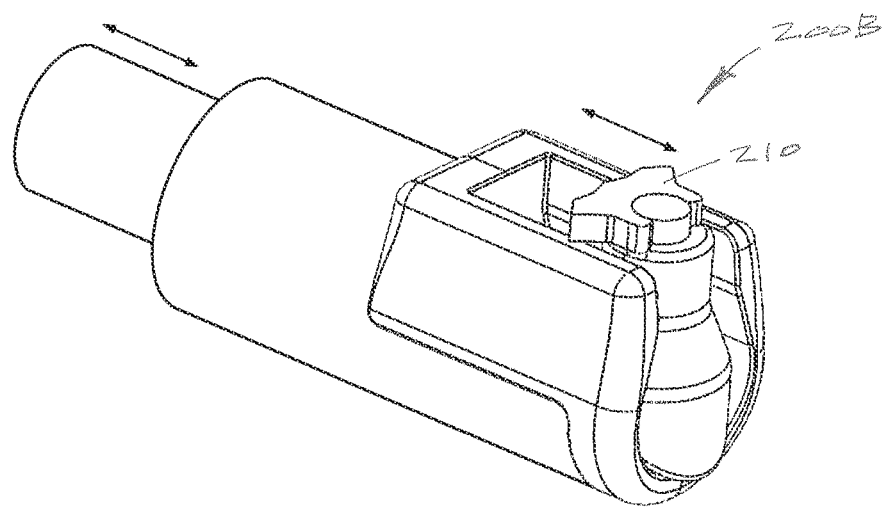
FIG. 5 is a perspective view of a working end of a variation of a probe that may be detachably coupled to the handpiece of FIG. 1, wherein the working end has a reciprocating electrode.
Figure 6:
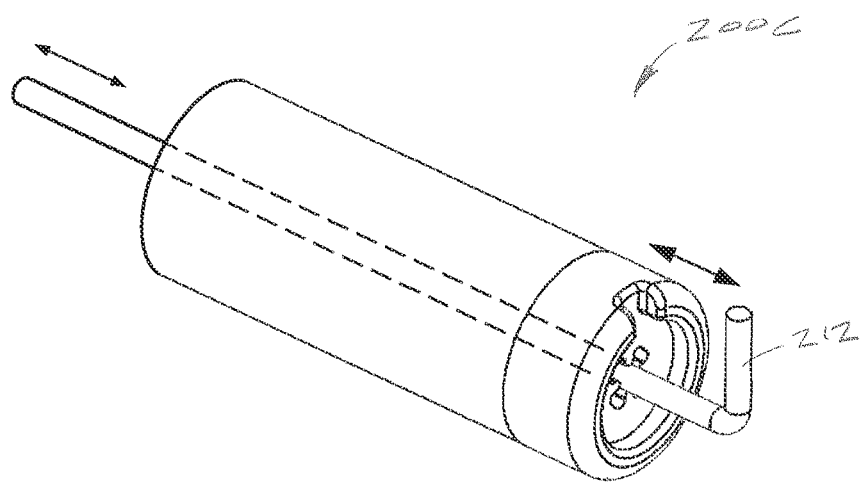
FIG. 6 is a perspective view of a working end of another variation of a probe that may be detachably coupled to the handpiece of FIG. 1, wherein the working end has a hook electrode that has extended and non-extended positions.
Figure 7:
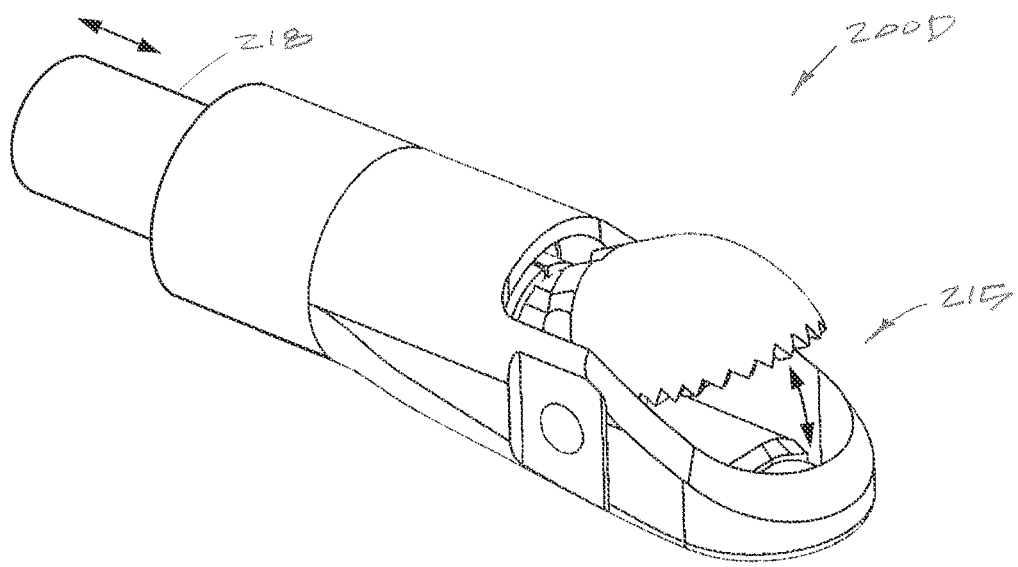
FIG. 7 is a perspective view of a working end of yet another variation of a probe that may be detachably coupled to the handpiece of FIG. 1, wherein the working end has an openable-closeable jaw structure for cutting tissue.

It can be understood from FIG. 1 that the system 100 and handpiece 104 is adapted for use with various disposable probes which can be designed for various different functions and procedures For example, FIG. 4 illustrates a different variation of a probe working end 200A that is similar to working end 112 of probe 110 of FIGS. 3A-3B, except the ceramic cutting member 205 extends distally from the outer sleeve 206 and the cutting member has burr edges 208 for cutting bone. The probe of FIG. 4 is described in more detail in co-pending and commonly owned patent application Ser. No. 15/271,184 filed Sep. 20, 2016 (Atty. Docket 41879-728.201) titled ARTHROSCOPIC DEVICES AND METHODS. FIG. 5 illustrates a different variation of a probe working end 200B with a reciprocating electrode 210 in a type of probe described in more detail in co-pending and commonly owned patent application Ser. No. 15/410,723 filed Jan. 19, 2017 titled ARTHROSCOPIC DEVICES AND METHODS. In another example, FIG. 6 illustrates another variation of a probe working end 200C that has an extendable-retractable hook electrode 212 in a probe type described in more detail in co-pending and commonly owned patent application Ser. No. 15/454,342 filed Mar. 9, 2017 titled ARTHROSCOPIC DEVICES AND METHODS. In yet another example. FIG. 7 illustrates a variation of a working end 200D in a probe type having an openable-closable jaw structure 215 actuated by reciprocating member 218 for trimming meniscal tissue or other tissue as described in more detail in co-pending and commonly owned patent application Ser. No. 15/483,940 filed Apr. 10, 2017 titled ARTHROSCOPIC DEVICES AND METHODS. All of the probes of FIGS. 4-7 can have a hub similar to hub 120 of probe 110 of FIG. 1 for coupling to the same handpiece 104 of FIG. 1, with some of the probes (see FIGS. 5-7) having a hub mechanism for converting rotational motion to linear motion. All of the patent applications just identified in this paragraph are incorporated herein by this reference.

FIG. 1 further shows that the system 100 also includes a negative pressure source 220 coupled to aspiration tubing 222 which communicates with a flow channel 224 in handpiece 104 and can cooperate with any of the probes 110, 200A, 200B or 200C of FIGS. 1-3B. 4, 5 and 6. In FIG. 1 it also can be seen that the system 100 includes an RF source 225 which can be connected to an electrode arrangement in any of the probes 110, 200A, 200B or 200C of FIGS. 1-3B, 4, 5 and 6. The controller 165 and microprocessor therein together with control algorithms are provided to operate and control all functionality, which includes controlling the motor drive 105 to move a motor-driven component of any probe working end 110, 200A, 200B or 200C, as well as for controlling the RF source 225 and the negative pressure source 220 which can aspirate fluid and tissue debris to collection reservoir 230.

As can be understood from the above description of the system 100 and handpiece 104, the controller 165 and controller algorithms need to be configured to perform and automate many tasks to provide for system functionality. In a first aspect, controller algorithms are needed for device identification so that when any of the different probes types 110, 200A, 200B, 200C or 200D of FIGS. 1 and 4-7 are coupled to handpiece 104, the controller 165 will recognize the probe type and then select algorithms for operating the motor drive 105. RF source 225 and negative pressure source 220 as is needed for the particular probe. In a second aspect, the controller is configured with algorithms that identify whether the probe is coupled to the handpiece 104 in an upward or downward orientation relative to the handpiece, wherein each orientation requires a different subset of the operating algorithms. In another aspect, the controller has separate control algorithms for each probe type wherein some probes have a rotatable cutter while others have a reciprocating electrode or jaw structure. In another aspect, most if not all the probes 110, 200A. 200B. 200C and 200D (FIGS. 1, 4-7) require a default "stop" position in which the motor-driven component is stopped in a particular orientation within the working end. For example, a rotatable cutter 145 with an electrode 155 needs to have the electrode centered within an outer sleeve window 158 in a default position such as depicted in FIG. 3B. Some of these systems, algorithms and methods of use are described next.

Figure 2B:
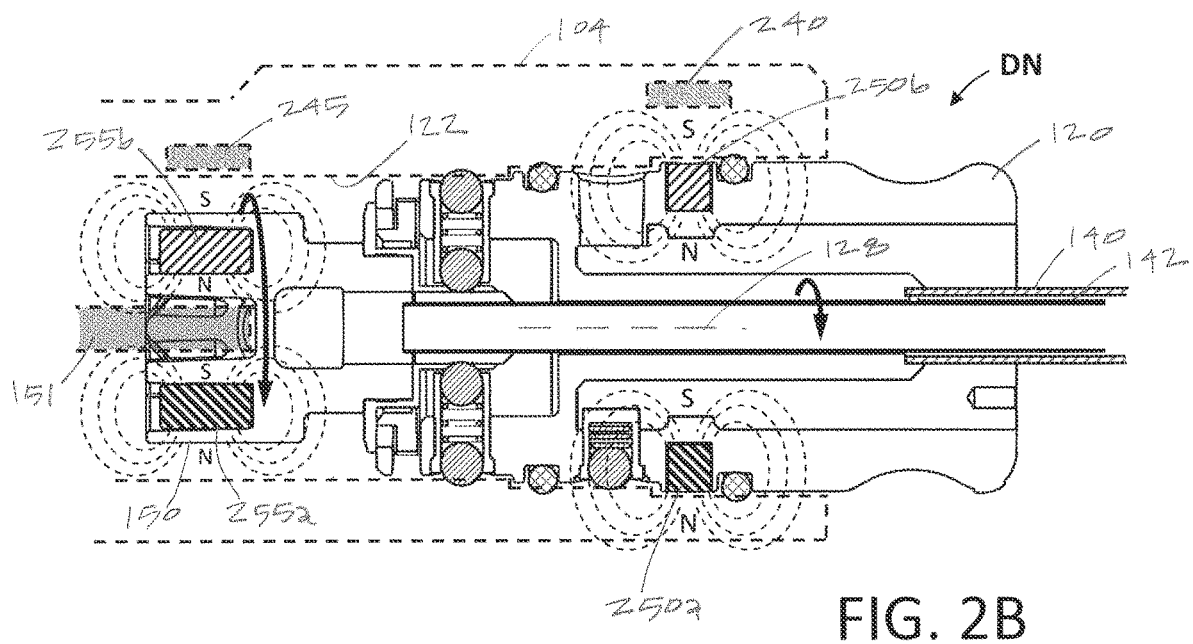
FIG. 2B is a sectional view of the hub of FIG. 1 taken along line 2B-2B of FIG. 1 with the hub and probe in a downward orientation relative to the handpiece showing the Hall effect sensor and magnets having a different orientation compared to that of FIG. 2A.

Referring to FIGS. 1 and 2A-2B, it can be seen that handpiece 104 carries a first Hall effect sensor 240 in a distal region of the handpiece 104 adjacent the receiving passageway 122 that receives the hub 120 of probe 110. FIG. 2A corresponds to the probe 110 and working end 112 in FIG. 1 being in the upward orientation indicated at UP. FIG. 2B corresponds to probe 110 and working end 112 in FIG. 1 being in the downward orientation indicated at DN. The handpiece 104 carries a second Hall effect sensor 245 adjacent the rotatable drive coupling 150 of the probe 110. The probe 110 carries a plurality of magnets as will be described below that interact with the Hall effect sensors 240, 245 to provide multiple control functions in cooperation with controller algorithms, including (i) identification of the type of probe coupled to the handpiece, (ii) the upward or downward orientation of the probe hub 120 relative to the handpiece 104, and (iii) the rotational position and speed of rotating drive collar 150 from which a position of either rotating or reciprocating motor-driven components can be determined.

The sectional views of FIGS. 2A-2B show that hub 120 of probe 110 carries first and second magnets 250a and 250b in a surface portion thereof. The Hall sensor 240 in handpiece 104 is in axial alignment with either magnet 250a or 250b when the probe hub 120 is coupled to handpiece 104 in an upward orientation (FIGS. 1 and 2A) or a downward orientation (FIGS. 1 and 2B). In one aspect as outlined above, the combination of the magnets 250a and 250b and the Hall sensor 240 can be used to identify the probe type. For example, a product portfolio may have from 2 to 10 or more types of probes, such as depicted in FIGS. 1 and 4-7, and each such probe type can carry magnets 250a. 250b having a specific, different magnetic field strength. Then, the Hall sensor 240 and controller algorithms can be adapted to read the magnetic field strength of the particular magnet(s) in the probe which can be compared to a library of field strengths that correspond to particular probe types. Then, a Hall identification signal can be generated or otherwise provided to the controller 165 to select the controller algorithms for operating the identified probe, which can include parameters for operating the motor drive 105, negative pressure source 220 and/or RF source 225 as may be required for the probe type. As can be seen in FIGS. 1, 2A and 2B, the probe hub 120 can be coupled to handpiece 104 in upward and downward orientations, in which the North (N) and South (S) poles of the magnets 250a, 250b are reversed relative to the probe axis 128. Therefore, the Hall sensor 240 and associated algorithms look for magnetic field strength regardless of polarity to identify the probe type.

Referring now to FIGS. 1, 2A-2B and 3A-3B, the first and second magnets 250a and 250b with their different orientations of North (N) and South (S) poles relative to central longitudinal axis 128 of hub 120 are also used to identify the upward orientation UP or the downward orientation DN of hub 120 and working end 112. In use, as described above, the physician may couple the probe 110 to the handpiece receiving passageway 122 with the working end 112 facing upward or downward based on his or her preference and the targeted tissue. It can be understood that controller algorithms adapted to stop rotation of the cutting member 145 in the window 158 of the outer sleeve 104 of working end 112 need to "learn" whether the working end is facing upward or downward, because the orientation or the rotating cutting member 145 relative to the handpiece and Hall sensor 240 would vary by 180°. The Hall sensor 240 together with a controller algorithm can determine the orientation UP or the downward orientation DN by sensing whether the North (N) or South (S) pole of either magnet 250a or 250b is facing upwardly and is proximate the Hall sensor 240.

In another aspect of the invention, in probe 110 (FIG. 1) and other probes, the motor-driven component of a working end, such as rotating cutter 145 of working end 112 of FIGS. 1 and 3A-3B needs to stopped in a selected rotational position relative to a cut-out opening or window 158 in the outer sleeve 140. Other probe types may have a reciprocating member or a jaw structure as described above, which also needs a controller algorithm to stop movement of a moving component in a selected position, such as the axial-moving electrodes of FIGS. 5-6 and the jaw structure of FIG. 7. In all probes, the motor drive 105 couples to the rotating drive coupling 150, thus sensing the rotational position of the drive coupling 150 can be used to determine the orientation of the motor-driven component in the working end. More in particular, referring to FIGS. 1 and 2A-2B, the drive coupling 150 carries third and fourth magnets 255a or 255b with the North (N) and South (S) poles of magnets 255a or 255b being reversed relative to the probe axis 128. Thus, Hall sensor 245 can sense when each magnet rotates passes the Hall sensor and thereby determine the exact rotational position of the drive coupling 150 twice on each rotation thereof (once for each magnet 255a, 255b). Thereafter, a controller tachometer algorithm using a clock can determine and optionally display the RPM of the drive coupling 150 and, for example, the cutting member 145 of FIG. 3A.

In another aspect of the invention, the Hall sensor 245 and magnets 255a and 255b (FIGS. 1 and 2A) are used in a set of controller algorithms to stop the rotation of a motor-driven component of a working end, for example, cutting member 145 of FIGS. 1 and 3A-3B in a pre-selected rotational position. In FIG. 3A, it can be seen that the inner sleeve 142 and a "first side" of cutting member 145 and window 154 therein is stopped and positioned in the center of window 158 of outer sleeve 140. The stationary position of cutting member 145 and window 154 in FIG. 3A may be used for irrigation or flushing of a working space to allow for maximum fluid outflow through the probe.

FIG. 3B depicts inner sleeve 142 and a "second side" of cutting member 145 positioned about the centerline of window 158 in the outer sleeve 140. The stationary or stopped position of cutting member 145 in FIG. 3B is needed for using the RF electrode 155 to ablate or coagulate tissue. It is important that the electrode 155 is maintained along the centerline of the outer sleeve window 158 since the outer sleeve 140 typically comprises return electrode 260. The position of electrode 155 in FIG. 3B is termed herein a "centerline default position". If the cutting member 145 and electrode 155 were rotated so as to be close to an edge 262a or 262b of window 158 in outer sleeve 140, RF current could arc between the electrodes 155 and 260 and potentially cause a short circuit disabling the probe. Therefore, a robust and reliable stop mechanism is required which is described next.

As can be understood from FIGS. 1 and 2A-2B, the controller 165 can always determine in real time the rotational position of drive coupling 150 and therefore the angular or rotational position of the ceramic cutting member 145 and electrode 155 can be determined. A controller algorithm can further calculate the rotational angle of the electrode 155 away from the centerline default position as the Hall sensor 245 can sense lessening of magnetic field strength as a magnet 255a or 255b in the drive coupling 150 rotates the electrode 155 away from the centerline default position. Each magnet has a specified, known strength and the algorithm can use a look-up table with that lists fields strengths corresponding to degrees of rotation away from the default position. Thus, if the Hall signal responsive to the rotated position of magnet 255a or 255b drops a specified amount from a known peak value in the centerline default position, it means the electrode 155 has moved away from the center of the window 158. In one variation, if the electrode 155 moves a selected rotational angle away from the centerline position during RF energy delivery to the electrode, the algorithm turns off RF current instantly and alerts the physician by an aural and/or visual signal, such as an alert on the LCD screen 170 on handpiece 104 and/or on a screen on a controller console (not shown). The termination of RF current delivery thus prevents the potential of an electrical arc between electrode 155 and the outer sleeve electrode 260.

It can be understood that during use, when the electrode 155 is in the position shown in FIG. 3B, the physician may be moving the energized electrode over tissue to ablate or coagulate tissue. During such use, the cutting member 145 and electrode 155 can engage or catch on tissue which inadvertently rotate the electrode 155 out of the default centerline position. Therefore, the system provides a controller algorithm, herein called an "active electrode monitoring" algorithm, wherein the controller continuously monitors position signals generated by Hall sensor 245 during RF energy delivery in both an ablation mode and a coagulation mode to determine if the electrode 155 and inner sleeve 142 have been bumped off the centerline position. In a variation, the controller algorithms can be configured to then re-activate the motor drive 105 to move the inner sleeve 142 and electrode 155 back to the default centerline position sleeve if electrode 155 had been bumped off the centerline position. In another variation, the controller algorithms can be configured to again automatically deliver RF current to RF electrode 155 when it is moved back to the to the default centerline position. Alternatively, the controller 165 can require the physician to manually re-start the delivery of RF current to the RF electrode 155 when it is moved back to the to the centerline position. In an aspect of the invention, the drive coupling 150 and thus magnets 255a and 255b are attached to inner sleeve 142 and cutting member 145 in a pre-determined angular relationship relative to longitudinal axis 128 so that the Hall sensor generates signals responsive to magnets 255a. 255b is the same for all probes within a probe type to thus allow the controller algorithm to function properly.

Figure 8:
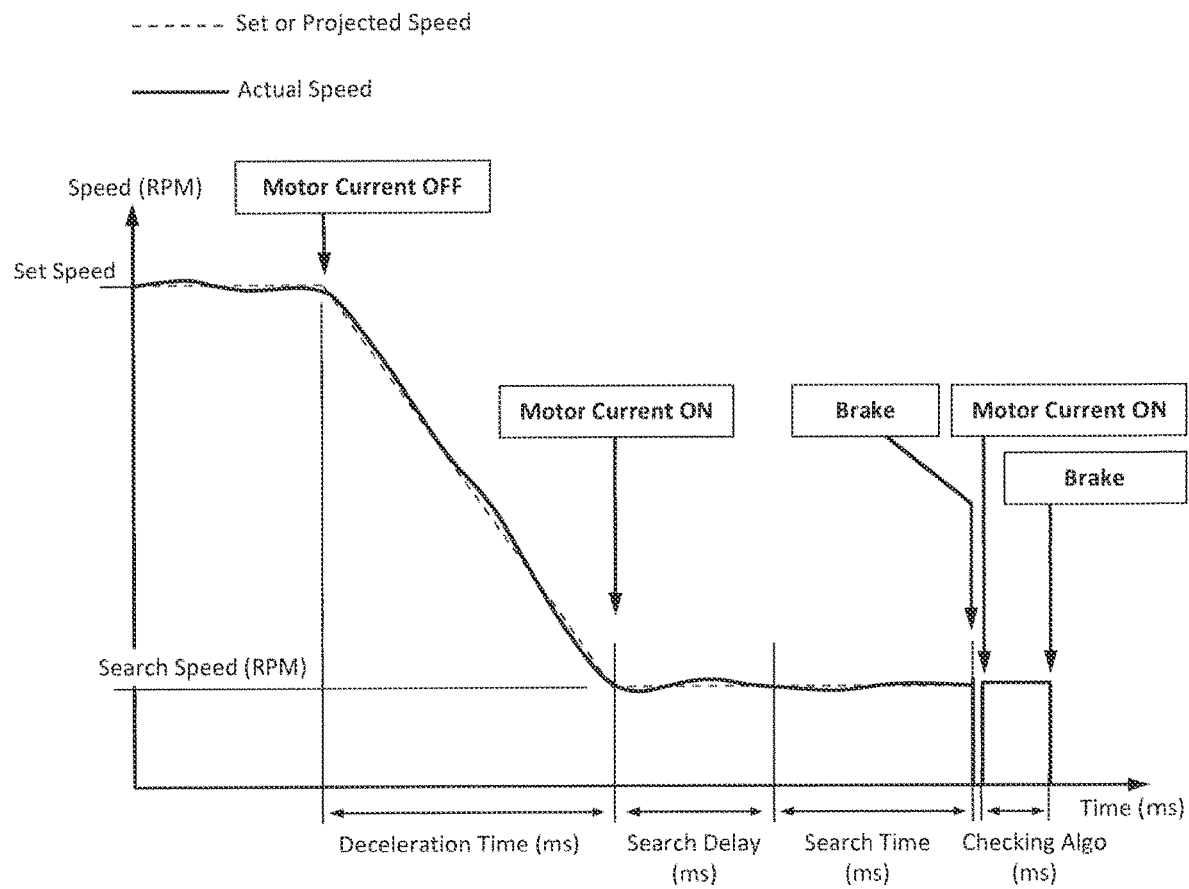
FIG. 8 is a chart relating to set speeds for a probe with a rotating cutting member as in FIGS. 1 and 3A that schematically shows the method used by a controller algorithm for stopping rotation of the cutting member in a selected default position.

Now turning to the stop mechanism or algorithms for stopping movement of a motor-driven component of working end 112, FIG. 8 schematically illustrates the algorithm and steps of the stop mechanism. In one variation, referring to FIG. 8, the stop mechanism corresponding to the invention uses (i) a dynamic braking method and algorithm to stop the rotation of the inner sleeve 142 and cutting member 145 (FIGS. 1, 3A-3B) in an initial position, and thereafter (ii) a secondary checking algorithm is used to check the initial stop position that was attained with the dynamic braking algorithm, and if necessary, the stop algorithm can re-activate the motor drive 105 to slightly reverse (or move forward) the rotation of drive coupling 150 and inner sleeve 142 as needed to position the cutting member 145 and electrode 155 within at the centerline position or within 0° to 5° of the targeted centerline default position. Dynamic braking is described further below. FIG. 8 schematically illustrates various aspects of controller algorithms for controlling the rotational speed of the cutting member and for stopping the cutting member 145 in the default centerline position.

In FIG. 8, it can be understood that the controller 165 is operating the probe 110 of FIGS. 1 and 3A-3B at a "set speed" which may be a PID controlled, continuous rotation mode in one direction or may be an oscillating mode where the motor drive 105 rotates the cutting member 145 in one direction and then reverses rotation as is known in the art. At higher rotational speeds such as 1,000 RPM to 20,000 RPM, it is not practical or feasible to acquire a signal from Hall sensor 245 that indicates the position of a magnet 255a or 255b in the drive coupling 150 to apply a stop algorithm. In FIG. 8, when the physician stop cutting with probe 110 by releasing actuation of an actuator button or foot pedal, current to the motor drive 105 is turned off. Thereafter, the controller algorithm uses the Hall sensor 245 to monitor deceleration of rotation of the drive coupling 150 and inner sleeve 142 until a slower RPM is reached. The deceleration period may be from 10 ms to 1 sec and typically is about 100 ms. When a suitable slower RPM is reached which is called a "search speed" herein (see FIG. 8), the controller 165 re-activates the motor drive 105 to rotate the drive coupling at a low speed ranging from 10 RPM to 1,000 RPM and in one variation is between 50 RPM and 250 RPM. An initial "search delay" period ranging from 50 ms to 500 ms is provided to allow the PID controller to stabilize the RPM at the selected search speed. Thereafter, the controller algorithm monitors the Hall position signal of magnet strength and when the magnet parameter reaches a predetermined threshold, for example, when the rotational position of drive coupling 150 and electrode 155 correspond to the centerline default position of FIG. 3B, the control algorithm then applies dynamic braking to instantly stop rotation of the motor drive shaft 151 drive coupling 150 and the motor-driven component of the probe. FIG. 8 further illustrates that the controller can check the magnet/drive coupling 150 position after the braking and stopping steps. If the Hall position signal indicates that the motor-driven component is out of the targeted default position, the motor drive 105 can be re-activated to move the motor-driven component and thereafter the brake can be applied again as described above.

Dynamic braking as shown schematically in FIG. 8 may typically stop the rotation of the drive coupling 150 with a variance of up to about 0°-15° of the targeted stop position, but this can vary even further when different types of tissue are being cut and impeding rotation of the cutting member 145, and also depending on whether the physician has completely disengaged the cutting member from the tissue interface when the motor drive is de-activated. Therefore, dynamic braking alone may not assure that the default or stop position is within a desired variance.

As background, the concept of dynamic braking is described in the following literature: https://www.ab.com/support/abdrives/documentation/techpapers/RegenOverview01.pdf and http://literature.rockwellautomation.com/idc/groups/literature/documents/wp/drives-wp004_-en-p/pdf. Basically, a dynamic braking system provides a chopper transistor on the DC bus of the AC PWM drive that feeds a power resistor that transforms the regenerative electrical energy into heat energy. The heat energy is dissipated into the local environment. This process is generally called dynamic braking with the chopper transistor and related control and components called the chopper module and the power resistor called the dynamic brake resistor. The entire assembly of chopper module with dynamic brake resistor is sometimes referred to as the dynamic brake module. The dynamic brake resistor allows any magnetic energy stored in the parasitic inductance of that circuit to be safely dissipated during the turn off of the chopper transistor.

The method is called dynamic braking because the amount of braking torque that can be applied is dynamically changing as the load decelerates. In other words, the braking energy is a function of the kinetic energy in the spinning mass and as it declines, so does the braking capacity. So the faster it is spinning or the more inertia it has, the harder you can apply the brakes to it, but as it slows, you run into the law of diminishing returns and at some point, there is no longer any braking power left.

In another aspect of the invention, a method has been developed to increase the accuracy of the stopping mechanism which is a component of the positioning algorithm described above. It has been found that each magnet in a single-use probe may vary slightly from its specified strength. As described above, the positioning algorithm uses the Hall effect sensor 245 to continuously monitor the field strength of magnets 255a and 255b as the drive coupling 150 rotates and the algorithm determines the rotational position of the magnets and drive coupling based on the field strength, with the field strength rising and falling as a magnet rotates past the Hall sensor. Thus, it is important for the algorithm to have a library of magnetic field strengths that accurately correspond to degrees of rotation away from a peak Hall signal when a magnet is adjacent the sensor 245. For this reason, an initial step of the positioning algorithm includes a "learning" step that allow the controller to learn the actual field strength of the magnets 255a and 255b which may vary from the specified strength. After a new single-use probe 110 (FIG. 1) is coupled to the handpiece 104, and after actuation of the motor drive 105, the positioning algorithm will rotate the drive coupling at least 180° and more often at least 360° while the Hall sensor 245 quantifies the field strength of the particular probe's magnets 255a and 255b. The positioning algorithm then stores the maximum and minimum Hall signals (corresponding to North and South poles) and calibrates the library of field strengths that correspond to various degrees of rotation away from a Hall min-max signal position when a magnet is adjacent the Hall sensor.

In general, a method of use relating to the learning algorithm comprises providing a handpiece with a motor drive, a controller, and a probe with a proximal hub configured for detachable coupling to the handpiece, wherein the motor drive is configured to couple to a rotating drive coupling in the hub and wherein the drive coupling carries first and second magnets with North and South poles positioned differently relative to said axis, and coupling the hub to the handpiece, activating the motor drive to thereby rotate the drive coupling and magnets at least 180°, using a handpiece sensor to sense the strength of each magnet, and using the sensed strength of the magnets for calibration in a positioning algorithm that is responsive to the sensor sensing the varying strength of the magnets in the rotating drive coupling to thereby increase accuracy in calculating the rotational position of the drive coupling 150.

Another aspect of the invention relates to an enhanced method of use using a probe working end with an electrode, such as the working end 112 of FIGS. 1 and 3B. As described above, a positioning algorithm is used to stop rotation of the electrode 155 in the default centerline position of FIG. 3B. An additional "slight oscillation" algorithm is used to activate the motor drive 105 contemporaneous with RF current to the electrode 155, particularly an RF cutting waveform for tissues ablation. The slight oscillation thus provides for a form of oscillating RF ablation. The slight oscillation algorithm rotates the electrode 155 in one direction to a predetermined degree of rotation, which the controller algorithms determine from the Hall position signals. Then, the algorithm reverses direction of the motor drive to rotate in the opposite direction until Hall position signals indicate that the predetermined degree of rotation was achieved in the opposite direction away from the electrode's default centerline position. The predetermined degree of angular motion can be any suitable rotation that is suitable for dimensions of the outer sleeve window, and in one variation is from 1° to 30° in each direction away from the centerline default position. More often, the predetermined degree of angular motion is from 5° to 15° in each direction away from the centerline default. The slight oscillation algorithm can use any suitable PID controlled motor shaft speed, and in one variation the motor shaft speed is from 50 RPM to 5,000 RPM, and more often from 100 RPM to 1,000 RPM. Stated another way, the frequency of oscillation can be from 20 Hz to 2,000 Hz and typically between 40 Hz and 400 Hz.

While the above description of the slight oscillation algorithm is provided with reference to electrode 155 on a rotating cutting member 145 of FIG. 3B, it should be appreciated that a reciprocating electrode 212 as shown in the working end 200C of FIG. 6 end could also be actuated with slight oscillation. In other words, the hook shape electrode 212 of FIG. 6 could be provided with a frequency of oscillation ranging from 20 Hz to 2,000 Hz and typically between 40 Hz and 400 Hz.

Figure 9A:
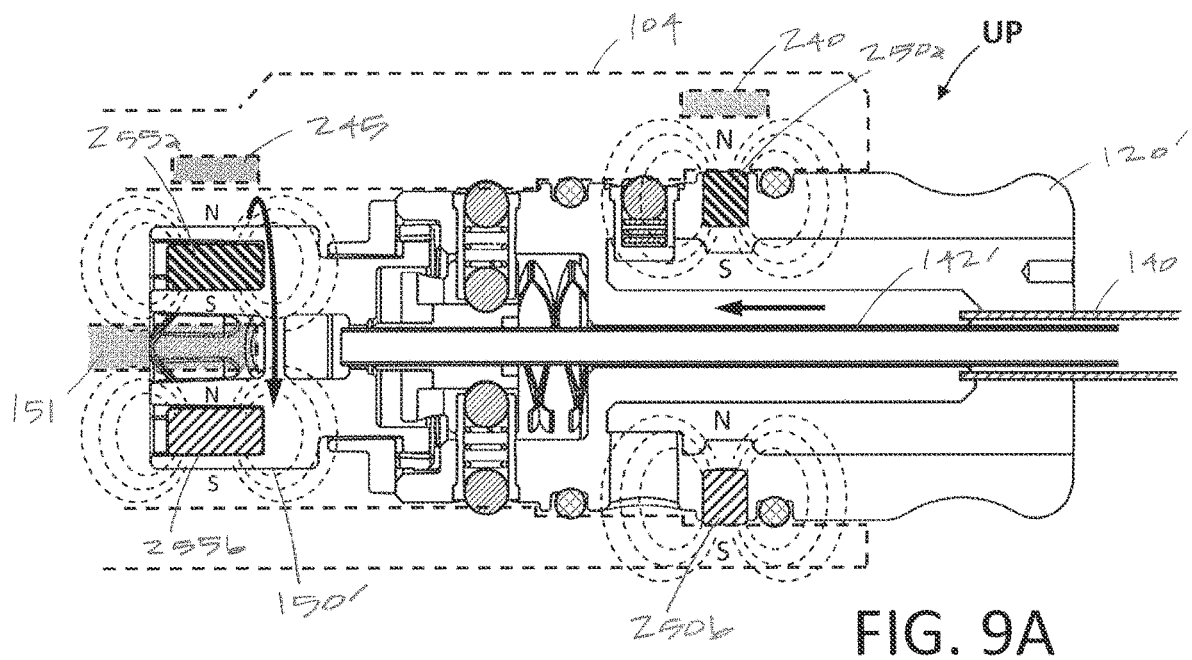
FIG. 9A is a longitudinal sectional view of a probe hub that is similar to that of FIG. 2A, except the hub of FIG. 9A has an internal cam mechanism for converting rotational motion to linear motion to axially reciprocate an electrode as in the working end of FIG. 5, wherein FIG. 9A illustrated the magnets in the hub and drive coupling are the same as in FIG. 2A and the hub is in an upward facing position relative to the handpiece.
Figure 9B:
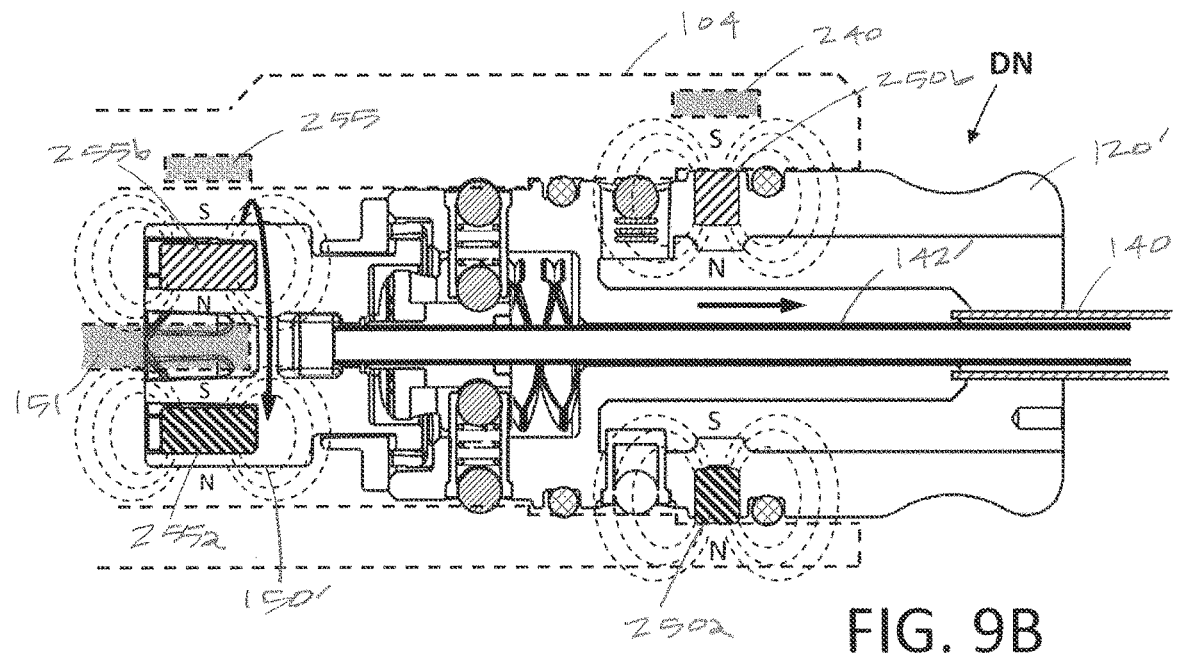
FIG. 9B is a sectional view of the hub of FIG. 9A rotated 180° in a downward facing position relative to the handpiece.

FIGS. 9A-9B are longitudinal sectional views of a probe hub 120' that corresponds to the working end 200B of FIG.

5 which has a reciprocating electrode 210. In FIGS. 9A-9B, the handpiece 104 and Hall affect sensors 240 and 245 are of course the same as described above as there is no change in the handpiece 104 for different types of probes. The probe hub 120' of FIGS. 9A-9B is very similar to the hub 120 of FIGS. 2A-2B with the first and second identification/orientation magnets 250a and 250b being the same. The third and fourth rotation al position magnets 255a and 255b also are the same and are carried by drive coupling 150'. The probe hub 120' of FIGS. 9A-9B only differs in that the drive coupling 150 rotates with a cam mechanism operatively coupled to inner sleeve 142' to convert rotational motion to linear motion to reciprocate the electrode 210 in working end 200B of FIG. 5. A similar hub for converting rotational motion to linear motion is provided for the working ends 200C and 200D of FIGS. 6 and 7, respectively, which each have a reciprocating component (212, 218) in its working end.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having." "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. An arthroscopic system, comprising:
   a controller;
   a handpiece operatively coupled to the controller, the handpiece including a motor drive and a first sensor; and
   a resecting probe with a proximal hub and an elongate shaft assembly that extends distally from the proximal hub about a longitudinal axis to a working end of the resecting probe, the elongate shaft assembly including an outer sleeve with an outer cutting window in a side of the outer sleeve, the outer cutting window communicating with an axial bore in the outer sleeve that extends proximally from outer cutting window back through the outer sleeve, the elongate shaft assembly further including an inner sleeve assembly that is rotatably received in the axial bore of the outer sleeve so that the inner sleeve assembly can achieve at least a first rotational position and a second rotational position in the outer sleeve, the inner sleeve assembly including a rotating drive coupling fixed to a proximal portion of the inner sleeve assembly, the inner sleeve assembly including a distal portion with an inner cutting window in a first side of the distal portion, the inner cutting window communicating with an axial extraction channel in the inner sleeve assembly that extends proximally from the inner cutting window back through the inner sleeve assembly for connecting to a negative pressure source, the distal portion of the inner sleeve assembly further including an electrode carried on a second side of the distal portion opposite the first side of the distal portion, the proximal hub detachably couplable to the handpiece to couple the rotating drive coupling to the motor drive for rotating the inner sleeve assembly in the outer sleeve,
   wherein, in the first rotational position, the inner cutting window aligns sufficiently with the outer cutting window to allow fluid outflow to pass through the outer cutting window and into the axial extraction channel through the inner cutting window during use, and
   wherein, in the second rotational position, the electrode aligns with a longitudinal centerline of the outer cutting window,
   wherein the proximal hub carries a first magnetic component including a first independent magnet and a second independent magnet that each have a North pole and a South pole, the first independent magnet and the second independent magnet being disposed in opposing sides of the proximal hub spaced outwardly from the longitudinal axis with the respective North poles of the first independent magnet and the second independent magnet oriented in opposite directions relative to the longitudinal axis, wherein the proximal hub is selectively couplable to the handpiece so that the working end of the resecting probe can be positioned for use in either an upward orientation or a downward orientation relative to a first side of the handpiece, wherein the first independent magnet is proximate the first sensor when the working end is in the upward orientation and the second independent magnet is proximate the first sensor when the working end is in the downward orientation;

wherein said controller is configured to receive a first signal from the first sensor about a magnetic field of the first independent magnet or the second independent magnet when the first independent magnet or the second independent magnet is proximate the first sensor to identify whether the working end is in said upward orientation or downward orientation relative to the first side of the handpiece.

2. The arthroscopic system of claim 1, wherein said controller is configured to receive a probe identification signal from the first sensor based on a strength of the magnetic field of the first independent magnet or the second independent magnet, wherein the probe identification signal correlates the strength of the magnetic field to a resecting probe type.

3. The arthroscopic system of claim 1, wherein the handpiece includes a second sensor.

4. The arthroscopic system of claim 3, wherein the rotating drive coupling includes a second magnetic component coupled thereto to rotate with the rotating drive coupling, the second magnetic component including a third independent magnet and a fourth independent magnet that each have a North pole and a South pole, the third independent magnet and the fourth independent magnet being disposed in opposing sides of the rotating drive coupling spaced outwardly from the longitudinal axis with the respective North poles of the third independent magnet and the fourth independent magnet oriented in opposite directions relative to the longitudinal axis.

5. The arthroscopic system of claim 4, wherein said controller is configured to receive a second signal from the second sensor about a magnetic field of the third independent magnet or the fourth independent magnet when the third independent magnet or the fourth independent magnet is proximate the second sensor to identify a rotational parameter of the rotating drive coupling.

6. The arthroscopic system of claim 5, wherein the rotational parameter of the rotating drive coupling is a rotational position of the rotating drive coupling.

7. The arthroscopic system of claim 5, wherein the rotational parameter of the rotating drive coupling is a rotational speed of the rotating drive coupling.

8. The arthroscopic system of claim 5, wherein said controller is configured to determine a rotational position of the rotating drive coupling using a positioning algorithm responsive to the second signal, wherein the second signal is based on sensing varying magnet parameters of the third independent magnet and the fourth independent magnet with the second sensor as the rotating drive coupling rotates.

9. The arthroscopic system of claim 8, wherein said controller is configured to de-activate the motor drive at a selected rotational position of the rotating drive coupling.

10. The arthroscopic system of claim 9, wherein said controller is configured to dynamically brake the motor drive to thereby stop rotation of the rotating drive coupling in a selected stop position.

11. The arthroscopic system of claim 4, wherein, along the longitudinal axis of the elongate shaft assembly of the resecting probe, the first independent magnet and the second independent magnet are located distally of the third independent magnet and the fourth independent magnet, and wherein, correspondingly in the handpiece, the first sensor is located distally of the second sensor.

12. The arthroscopic system of claim 4, wherein said second sensor is configured to sense varying strengths of the third independent magnet and the fourth independent magnet as the rotating drive coupling rotates, and where said controller is configured to calibrate a rotational position of the rotating drive coupling responsive to the varying strength of the third independent magnet and the fourth independent magnet to thereby increase accuracy in calculating the sensed strength of the third independent magnet and the fourth independent magnet.

13. The arthroscopic system of claim 4, wherein, in the inner sleeve assembly, the second magnetic component is in a fixed predetermined rotational position relative to the electrode.

14. The arthroscopic system of claim 1, wherein said controller is configured to use a controller algorithm for operating the resecting probe based on the identified upward orientation or downward orientation of the working end of the resecting probe.

15. The arthroscopic system of claim 1, wherein the inner sleeve assembly includes a metal inner sleeve.

16. The arthroscopic system of claim 15, wherein the inner sleeve assembly includes a ceramic cutting member that is disposed at a distal end of the metal inner sleeve to provide the distal portion of the inner sleeve assembly.

* * * * *